US010328386B2

(12) United States Patent
Liu et al.

(10) Patent No.: US 10,328,386 B2
(45) Date of Patent: Jun. 25, 2019

(54) CO-CAST THIN FILM COMPOSITE FLAT SHEET MEMBRANES FOR GAS SEPARATIONS AND OLEFIN/PARAFFIN SEPARATIONS

(71) Applicant: UOP LLC, Des Plaines, IL (US)

(72) Inventors: Chunqing Liu, Arlington Heights, IL (US); Carl W. Liskey, Chicago, IL (US); Nicole K. Karns, Chicago, IL (US)

( * ) Notice: Subject to any disclaimer, the term of this patent is extended or adjusted under 35 U.S.C. 154(b) by 74 days.

(21) Appl. No.: 15/599,258

(22) Filed: May 18, 2017

(65) Prior Publication Data

US 2018/0333675 A1    Nov. 22, 2018

(51) Int. Cl.
| | |
|---|---|
| B01D 69/02 | (2006.01) |
| B01D 53/22 | (2006.01) |
| B01D 71/64 | (2006.01) |
| B01D 71/68 | (2006.01) |
| B01D 71/02 | (2006.01) |
| B01D 69/12 | (2006.01) |
| B01D 67/00 | (2006.01) |
| C07C 7/144 | (2006.01) |
| B01D 69/14 | (2006.01) |
| B01D 71/10 | (2006.01) |
| B01D 71/76 | (2006.01) |

(52) U.S. Cl.
CPC ....... *B01D 53/228* (2013.01); *B01D 67/0013* (2013.01); *B01D 69/02* (2013.01); *B01D 69/12* (2013.01); *B01D 69/148* (2013.01); *B01D 71/022* (2013.01); *B01D 71/64* (2013.01); *B01D 71/68* (2013.01); *C07C 7/144* (2013.01); *B01D 67/0016* (2013.01); *B01D 67/0088* (2013.01); *B01D 71/10* (2013.01); *B01D 71/76* (2013.01); *B01D 2323/12* (2013.01); *B01D 2323/30* (2013.01); *B01D 2323/345* (2013.01); *B01D 2325/023* (2013.01)

(58) Field of Classification Search
None
See application file for complete search history.

(56) References Cited

U.S. PATENT DOCUMENTS

| | | | |
|---|---|---|---|
| 3,133,132 A | 5/1964 | Sidney et al. | |
| 5,198,316 A | 3/1993 | Wernet et al. | |
| 5,256,295 A | 10/1993 | Baker et al. | |
| 5,670,051 A | 9/1997 | Pinnau | |
| 6,180,008 B1 * | 1/2001 | White | B01D 61/02 208/308 |
| 6,932,589 B2 | 8/2005 | Suzuki | |
| 7,048,846 B2 | 5/2006 | White et al. | |
| 7,125,935 B2 | 10/2006 | Andrews et al. | |
| 7,361,800 B2 * | 4/2008 | Herrera | B01D 53/228 585/809 |
| 7,803,275 B2 | 9/2010 | Partridge et al. | |
| 8,173,323 B2 | 5/2012 | An et al. | |
| 8,337,598 B2 * | 12/2012 | Yates | B01D 67/009 55/527 |
| 8,366,804 B2 | 2/2013 | Liu et al. | |
| 8,561,812 B2 | 10/2013 | Liu et al. | |
| 8,574,785 B2 | 11/2013 | Kim et al. | |
| 8,829,059 B2 | 9/2014 | Wynn et al. | |
| 8,912,288 B2 | 12/2014 | Liu et al. | |
| 9,017,451 B2 | 4/2015 | Wynn et al. | |
| 9,126,152 B2 | 9/2015 | Liu et al. | |
| 9,126,154 B2 | 9/2015 | Liu et al. | |
| 9,126,156 B2 | 9/2015 | Liu et al. | |
| 9,211,508 B2 | 12/2015 | Liu et al. | |
| 9,216,390 B2 | 12/2015 | Ho et al. | |
| 9,751,050 B2 | 9/2017 | Zhou et al. | |
| 10,258,929 B2 | 4/2019 | Liu et al. | |
| 2004/0154980 A1 | 8/2004 | Kim et al. | |
| 2004/0215045 A1 | 10/2004 | Herrera et al. | |
| 2006/0000778 A1 | 1/2006 | Childs et al. | |
| 2007/0190385 A1 | 8/2007 | Lee et al. | |
| 2008/0063917 A1 | 3/2008 | Yamashita et al. | |
| 2008/0268314 A1 | 10/2008 | Han et al. | |
| 2009/0277837 A1 | 11/2009 | Liu et al. | |
| 2010/0018926 A1 | 1/2010 | Liu et al. | |
| 2010/0147148 A1 | 6/2010 | Rabiei | |
| 2011/0094960 A1 | 4/2011 | Zhou et al. | |

(Continued)

FOREIGN PATENT DOCUMENTS

| | | |
|---|---|---|
| CN | 103402614 A | 11/2013 |
| CN | 104275094 A | 1/2015 |

(Continued)

OTHER PUBLICATIONS

Riley, "Thin-Film Composite Membrane for Single-Stage Seawater Desalination by Reverse Osmosis", Applied Polymer Symposium No. 22, pp. 255-267 (1973).
Chen, "Bioinspired fabrication of composite pervaporation membranes with high permeation flux and structural stability", Journal of Membrane Science 344 (2009) 136-143.
Ma, "High-flux thin-film nanofibrous composite ultrafiltration membranes containing cellulose barrier layer", J. Mater. Chem., 2010, 20, 4692-4704 (2010).
Wanichapichart, Characteristics of polyethersulfone/chitosan composite membranes:, Biophysics Unit, Membrane Science and Technology Research Center, Faculty of Science, Prince of Songkia University, Had Yai, Songkhla, Thailand 90112.

(Continued)

*Primary Examiner* — Tam M Nguyen

(57) ABSTRACT

A co-cast thin film composite flat sheet membrane is provided that comprises an asymmetric porous non-selective support layer with a thickness of 10-50 micrometers and an asymmetric integrally skinned polyimide-containing selective layer with a thickness of 5-40 micrometers on top of said support layer, wherein said asymmetric integrally skinned polyimide-containing selective layer comprises a porous non-selective polyimide-containing support layer with a thickness of ~5-40 micrometers and a relatively porous, thin, dense, polyimide-containing top skin layer with a thickness of 0.02-0.2 micrometers.

10 Claims, No Drawings

(56) References Cited

U.S. PATENT DOCUMENTS

| | | |
|---|---|---|
| 2012/0031833 A1 | 2/2012 | Ho et al. |
| 2012/0285881 A1 | 11/2012 | Jikihara et al. |
| 2013/0255483 A1 | 10/2013 | Sanders et al. |
| 2013/0299428 A1 | 11/2013 | Bikel et al. |
| 2013/0233791 A1 | 12/2013 | Koo et al. |
| 2014/0137734 A1 | 5/2014 | Liu et al. |
| 2014/0290478 A1 | 10/2014 | Liu et al. |
| 2015/0025293 A1 | 1/2015 | Feiring et al. |
| 2015/0053079 A1 | 2/2015 | Koros et al. |
| 2015/0068978 A1 | 3/2015 | Lando et al. |
| 2015/0098872 A1 | 4/2015 | Kelly et al. |
| 2015/0343398 A1* | 12/2015 | Aamer .................. B01D 71/80 210/500.28 |
| 2016/0107127 A1 | 4/2016 | Lee et al. |
| 2016/0114296 A1* | 4/2016 | Weber ................ B01D 67/0006 210/650 |
| 2016/0177035 A1 | 6/2016 | Liu et al. |
| 2016/0325229 A1 | 11/2016 | Zhou et al. |
| 2017/0291143 A1 | 10/2017 | Zhou et al. |
| 2017/0354918 A1 | 12/2017 | Liu et al. |
| 2018/0001277 A1 | 1/2018 | Liu et al. |
| 2018/0154311 A1 | 6/2018 | Zhou et al. |
| 2018/0333675 A1 | 11/2018 | Liu et al. |
| 2018/0345230 A1 | 12/2018 | Karns et al. |
| 2019/0060841 A1 | 2/2019 | Liu et al. |

FOREIGN PATENT DOCUMENTS

| | | |
|---|---|---|
| EP | 458598 A2 | 11/1991 |
| EP | 1375459 A1 | 1/2004 |
| EP | 2545985 A1 | 1/2013 |
| EP | 2764908 A1 | 8/2014 |
| WO | 2009002747 A2 | 12/2008 |

OTHER PUBLICATIONS

PCT Search Report dated Nov. 29, 2018 for PCT Appl. No. PCT/US2018/047547.

Hess et al., Prpene/prpane separation with copolyimide membranes containing silver ions, Journal of Membrane Science, vol. 275, issue 1-2, Apr. 20, 2006, pp. 52-60.

PCT Search Report dated Sep. 14, 2017 for PCT Application No. PCT/US2017/038294.

Kang, "Novel Application of Partially Positively Charged Silver Nanoparticles for Facilitated Transport in Olefin/Paraffin Separation Membranes", Chem. Mater. 2008, 20, 1308-1311.

PCT Search Report dated Oct. 5, 2017 for PCT Appl. No. PCT/US2017/038307.

PCT Search Report dated Aug. 30, 2018 for PCT Appl. No. PCT/US2018/032251.

PCT Search Report dated Sep. 14, 2017 for PCT Appl. No. PCT/US2017/036265.

Kudinov, "Separation Characteristics of an Ejector Membrane-Sorption Hybrid System", Theoretical Foundations of Chemical Engineering, 2014, vol. 48, No. 6, 832-836, Pleiades Publishing, Ltd., 2014.

PCT Search Report dated Aug. 30, 2018 for PCT Appl. No. PCT/US2018/035004.

* cited by examiner

CO-CAST THIN FILM COMPOSITE FLAT SHEET MEMBRANES FOR GAS SEPARATIONS AND OLEFIN/PARAFFIN SEPARATIONS

BACKGROUND OF THE INVENTION

Membrane-based technologies have advantages of both low capital cost and high-energy efficiency compared to conventional separation methods. Polymeric membranes have proven to operate successfully in industrial gas separations such as in the separation of nitrogen from air and the separation of carbon dioxide from natural gas. Cellulose acetate (CA) commercial spiral wound and hollow fiber membranes have been used extensively for natural gas upgrading. However, CA membranes still need improvement in a number of properties including selectivity, performance durability, chemical stability, resistance to hydrocarbon contaminants, resistance to solvent swelling, and resistance to $CO_2$ plasticization. Natural gas often contains substantial amounts of heavy hydrocarbons and water, either as an entrained liquid, or in vapor form, which may lead to condensation within membrane modules. The gas separation capabilities of CA membranes are affected by contact with liquids including water and aromatic hydrocarbons such as benzene, toluene, ethylbenzene, and xylene (collectively known as BTEX). The presence of more than modest levels of liquid BTEX heavy hydrocarbons is potentially damaging to the CA membrane. Therefore, precautions must be taken to remove the entrained liquid water and heavy hydrocarbons upstream of the membrane separation steps using expensive membrane pretreatment system. Another issue of CA polymer membranes that still needs to be addressed for their use in gas separations in the presence of high concentration of condensable gas or vapor such as carbon dioxide ($CO_2$) and propylene is the plasticization of the polymer by these condensable gases or vapors that leads to swelling of the membrane as well as a significant increase in the permeance of all components in the feed and a decrease in the selectivity of CA membranes. For example, the permeation behavior of $CO_2$ in CA membranes is different when compared to some other glassy polymers in that above a certain pressure level, the permeability coefficient begins to increase with pressure due to the onset of plasticization by the $CO_2$. A high concentration of sorbed $CO_2$ leads to increased segmental motion, and, consequently, the transport rate of the penetrant is enhanced. The challenge of treating gas, such as natural gas, that contains relatively large amounts of $CO_2$, such as more than about 50%, is particularly difficult.

In addition, some natural gas feed has high $CO_2/C_{2+}$ concentration (usually $CO_2$>70%). Membranes can be used to recover the high value natural gas liquid while removing $CO_2$ from natural gas. Membranes can separate $CO_2$ from $CH_4$ and $C_{2+}$ and recover $C_{2+}$ from the membrane retentate. When using membranes for this separation, the feed side temperature drops significantly due to $CO_2$ permeation (J-T effect), and the feed gas dew point increases as $CO_2$ permeates, therefore liquid comes out from membrane system. The membranes, however, show significantly decreased membrane permeance in the presence of liquid aliphatic hydrocarbons, liquid aromatics, or both liquid aliphatic hydrocarbons and liquid aromatics.

Therefore, new robust membranes with stable performance under repetitive short term exposure to liquid hydrocarbon condensation, high resistance to hydrocarbon contaminants, high resistance to solvent swelling, and high resistance to $CO_2$ plasticization are desired for natural gas upgrading.

Polymeric membrane materials have been found to be of use in gas separations. Numerous research articles and patents describe polymeric membrane materials (e.g., polyimides, polysulfones, polycarbonates, polyethers, polyamides, polyarylates, polypyrrolones) with desirable gas separation properties, particularly for use in oxygen/nitrogen separation (see, for example, U.S. Pat. No. 6,932,589). The polymeric membrane materials are typically used in processes in which a feed gas mixture contacts the upstream side of the membrane, resulting in a permeate mixture on the downstream side of the membrane with a greater mole fraction of one of the components than the composition of the original feed gas mixture. A pressure differential is maintained between the upstream and downstream sides, providing the driving force for permeation. The downstream side can be maintained as a vacuum, or at any pressure below the upstream pressure.

The membrane performance is characterized by the flux of a gas component across the membrane. This flux can be expressed as a quantity called the permeability (P), which is a pressure- and thickness-normalized flux of a given component. The separation of a gas mixture is achieved by a membrane material that permits a faster permeation rate for one component (i.e., higher permeability) over that of another component. The efficiency of the membrane in enriching a component over another component in the permeate stream can be expressed as a quantity called selectivity. Selectivity can be defined as the ratio of the permeabilities of the gas components across the membrane (i.e., $P_A/P_B$, where A and B are the two components). A membrane's permeability and selectivity are material properties of the membrane material itself, and thus these properties are ideally constant with feed pressure, flow rate and other process conditions. However, permeability and selectivity are both temperature-dependent. It is desired to develop membrane materials with a high selectivity (efficiency) for the desired component, while maintaining a high permeability (productivity) for the desired component.

The relative ability of a membrane to achieve the desired separation is referred to as the separation factor or selectivity for the given mixture. There are however several other obstacles to use a particular polymer to achieve a particular separation under any sort of large scale or commercial conditions. One such obstacle is permeation rate or flux. One of the components to be separated must have a sufficiently high permeation rate at the preferred conditions or extraordinarily large membrane surface areas are required to allow separation of large amounts of material. Therefore, commercially available polymer membranes, such as CA, polyimide, and polysulfone membranes formed by phase inversion and solvent exchange methods have an asymmetric integrally skinned membrane structure. See U.S. Pat. No. 3,133, 132. Such membranes are characterized by a thin, dense, selectively semipermeable surface "skin" and a less dense void-containing (or porous), non-selective support region, with pore sizes ranging from large in the support region to very small proximate to the "skin". The thin dense skin layer and the porous non-selective support layer are formed simultaneously from the same polymeric material. Therefore, the cost of a new asymmetric integrally skinned polymeric membrane could be very high when an expensive new polymeric membrane material is used. One attempt at reducing the cost of the new membranes has been the development of thin film composite (TFC) membranes, comprising a thin selective skin layer of a high cost, high performance polymer deposited on a porous, low cost, non-selective support membrane. See, for example, "Thin-Film Composite Membrane for Single-Stage Seawater Desalination by Reverse Osmosis" by R. L. Riley et al., Applied Polymer Symposium No. 22, pages 255-267 (1973). TFC membranes can be formed from CA, polysulfone, polyethersulfone, polyamide, polyimide, polyetherimide, cellulose nitrate, polyurethane, polycarbonate, polystyrene, etc. TFC hollow fiber membranes can be fabricated via a one-step co-extrusion process using two different polymeric spinning solutions and a triple-annular spinneret. For example, U.S. Pat. No. 8,337,598 disclosed a TFC hollow fiber membrane with a core cheap polymer layer and a sheath polyimide polymer layer. However, fabrication of TFC flat sheet membranes that are free from leaks is difficult, and normally fabrication requires multiple steps and so is generally more complex and costly. For example, TFC flat sheet membranes reported in the literature are typically formed by first fabricating a porous asymmetric integrally skinned polymeric membrane via a phase inversion technique followed by adding a thin selective layer on top of the porous asymmetric integrally skinned polymeric membrane by coating, laminating, interfacial polymerization, or other method.

Light olefins, such as propylene and ethylene, are produced as co-products from a variety of feedstocks in a number of different processes in the chemical, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by cryogenic distillation, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have the advantages of both low capital cost and high-energy efficiency compared to conventional separation methods for olefin/paraffin separations, such as propylene/propane and ethylene/ethane separations. Four main types of membranes have been reported for olefin/paraffin separations. These are facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability, due to carrier poisoning or loss, high cost, and low flux, currently limit practical applications of facilitated transport membranes.

Separation of olefins from paraffins via conventional polymer membranes has not been commercially successful due to inadequate selectivities and permeabilities of the polymer membrane materials, as well as due to plasticization issues. Polymers that are more permeable are generally less selective than are less permeable polymers. A general trade-off has existed between permeability and selectivity (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

More efforts have been undertaken to develop metal ion incorporated, high olefin/paraffin selectivity facilitated transport membranes. The high selectivity for olefin/paraffin separations is achieved by the incorporation of metal ions such as silver (I) or copper (I) cations into the solid nonporous polymer matrix layer on top of the highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes and the fixed site carrier facilitated transport membranes are less sensitive to the loss of metal cation carriers than the supported liquid facilitated transport membranes.

U.S. Pat. No. 5,670,051 (Pinnau et al.) disclosed a solid polymer electrolyte fixed site carrier facilitated transport membrane comprising silver tetrafluoroborate incorporated poly(ethylene oxide). U.S. Pat. No. 7,361,800 (Herrera et al.) disclosed a process for the separation of olefin/paraffin mixtures using a silver cation-cheated chitosan fixed site carrier facilitated transport membrane. U.S. Pat. No. 7,361,800 disclosed the coating of a layer of chitosan on the surface of a microporous support membrane, wherein the support membrane is made from polyesters, polyamides, polyimides, polyvinylidene fluoride, polyacrylonitrile, polysulfones or polycarbonates.

US 2015/0025293 A1 (Feiring et al.) disclosed a new facilitated transport membrane comprising silver (I) cation exchanged fluorinated copolymer synthesized from a perfluorinated cyclic or cyclizable monomer and a strong acid highly fluorinated vinylether compound.

The composite facilitated transport membranes disclosed in the literature comprise an ultrafiltration or microfiltration membrane as the support membrane. The use of a TFC flat sheet membrane comprising a high performance polymeric selective layer and a cheap, porous, non-selective support layer for the preparation of fixed site carrier facilitated transport membranes for olefin/paraffin separations has not been reported in the literature.

SUMMARY OF THE INVENTION

The present invention discloses a new co-cast thin film composite (TFC) flat sheet membrane comprising an asymmetric porous non-selective support layer with a thickness of 10-50 micrometers and an asymmetric integrally skinned polyimide-containing selective layer with a thickness of 5-40 micrometers on top of the support layer, wherein the asymmetric integrally skinned polyimide-containing selective layer comprises a porous non-selective polyimide-containing support layer with a thickness of about 5-40 micrometers and a relatively porous, thin, dense, polyimide-containing top skin layer with a thickness of 0.02-0.2 micrometers. In some cases, the co-cast TFC flat sheet membrane described in the present invention further comprises a hydrophobic fluoropolymer coating layer with a thickness of 0.02-1 micrometers on top of the relatively porous, thin, dense, polyimide-containing top skin layer for gas separations. In some cases, the relatively porous, thin, dense, polyimide-containing top skin layer of the co-cast TFC comprising hydrophobic fluoropolymer coating layer described in the present invention is further cross-linked under UV radiation to improve the selectivity. In some cases, the co-cast TFC flat sheet membrane further comprises a hydrophilic polymer and a metal salt inside the pores on the relatively porous, thin, dense, polyimide-containing top skin layer for olefin/paraffin separations. This invention also includes a method of making the co-cast TFC flat sheet membrane, and the use of such a membrane for gas separations and olefin/paraffin separations such as natural gas liquid (NGL) recovery and $CO_2$ removal from natural gas in one-step fuel gas conditioning, hydrogen recovery, natural gas upgrading applications such as off-shore gas-processing platforms, floating liquefied natural gas (FLNG), and floating, processing, storage and offloading (FPSO) vessel applications, as well as propylene/propane ($C_3=/C_3$) and ethylene/ethane ($C_2=/C_2$) separations.

The new co-cast TFC flat sheet membrane described in the present invention comprises an asymmetric porous non-selective support layer and an asymmetric integrally skinned polyimide-containing selective layer on top of the support layer wherein the asymmetric porous non-selective support layer comprises a non-polyimide polymer or a mixture of a non-polyimide polymer and a polyimide polymer wherein the weight ratio of the non-polyimide polymer to the polyimide polymer in the mixture is in a range of 20:1 to 2:1.

The co-cast TFC flat sheet membrane described in the present invention comprises an asymmetric porous non-selective support layer and an asymmetric integrally skinned polyimide-containing selective layer on top of the support layer wherein the asymmetric integrally skinned polyimide-containing selective layer comprises a polyimide polymer or a mixture of a non-polyimide polymer and a polyimide polymer wherein the weight ratio of the non-polyimide polymer to the polyimide polymer in the mixture is in a range of 10:1 to 1:10.

The co-cast TFC flat sheet membrane is fabricated by simultaneously co-casting a polymer solution for the formation of the asymmetric porous non-selective support layer and a different polymer solution for the formation of the asymmetric integrally skinned polyimide-containing selective layer on top of the support layer using two casting knives via a phase inversion process.

The co-cast TFC flat sheet membrane allows the use of higher cost, high performance polyimide polymer to form the asymmetric integrally skinned polyimide-containing selective layer and the use of less costly, commercially available polymers to form the asymmetric porous non-selective support layer without any potential delamination issue. Therefore, the new co-cast TFC flat sheet membrane has a reduced cost compared to the asymmetric integrally-skinned, flat sheet, higher cost, high performance polymer membranes.

The non-polyimide polymer in the asymmetric porous non-selective support layer and in the asymmetric integrally skinned polyimide-containing selective layer of the new co-cast TFC flat sheet membrane is selected from any relatively inexpensive, commercially available polymeric material such as polysulfone, polyethersulfone, polyetherimide, cellulose acetate, cellulose triacetate, cellulose nitrate, polyacrylonitrile, and mixtures thereof. The non-polyimide polymer in the asymmetric porous non-selective support layer and the non-polyimide polymer in the asymmetric integrally skinned polyimide-containing selective layer of the co-cast TFC flat sheet membrane can be selected from the same polymer or different polymers. Preferably, the non-polyimide polymer in the asymmetric porous non-selective support layer and the non-polyimide polymer in the asymmetric integrally skinned polyimide-containing selective layer of the new co-cast TFC flat sheet membrane described in the present invention are polyethersulfone.

The co-cast TFC flat sheet membrane with a hydrophobic fluoropolymer coating layer and cross-linked under UV radiation has the advantages of low cost, high selectivity, as well as stable permeance (or flux) and sustained selectivity over time by resistance to solvent swelling, plasticization and liquid hydrocarbon contaminants for gas separation applications. The co-cast TFC flat sheet membrane with a hydrophilic polymer and a metal salt inside the pores on the relatively porous, thin, dense, polyimide-containing top skin layer has advantages of low cost, high selectivity, and stable permeance (or flux) for olefin/paraffin separations.

The present invention also discloses a process of using the new co-cast TFC flat sheet membrane for gas separations and olefin/paraffin separations such as natural gas liquid (NGL) recovery and $CO_2$ removal from natural gas in one-step, fuel gas conditioning, hydrogen recovery, natural gas upgrading applications such as off-shore gas-processing platforms, floating liquefied natural gas (FLNG), and floating, processing, storage and offloading (FPSO) vessel applications, as well as propylene/propane ($C_3=/C_3$) and ethylene/ethane ($C_2=/C_2$) separations. The invention provides a process for separating at least one gas from a mixture of gases using the co-cast TFC flat sheet membrane with a hydrophobic fluoropolymer coating layer and cross-linked under UV radiation, the process comprising: (a) providing a co-cast TFC flat sheet membrane with a hydrophobic fluoropolymer coating layer and cross-linked under UV radiation which is permeable to at least one gas; (b) contacting the mixture on one side of the co-cast TFC flat sheet membrane with a hydrophobic fluoropolymer coating layer and cross-linked under UV radiation to cause at least one gas to permeate the membrane; and (c) removing from the opposite side of the membrane a permeate gas composition comprising a portion of the at least one gas which permeated the membrane.

DETAILED DESCRIPTION OF THE INVENTION

The use of membranes for separation of both gases and liquids is a growing technological area with potentially high economic reward due to the low energy requirements and the potential for scaling up of modular membrane designs. Advances in membrane technology, with the continuing development of new membrane materials will make this technology even more competitive with traditional, high-energy intensive and costly processes such as distillation. Among the applications for large scale gas separation membrane systems are nitrogen enrichment, oxygen enrichment, hydrogen recovery, removal of hydrogen sulfide and carbon dioxide from natural gas and dehydration of air and natural gas. Also, various hydrocarbon separations are potential applications for the appropriate membrane system. The materials that are used in these applications must have high selectivity, durability, and productivity in processing large volumes of gas or vapor in order to be economically successful. Membranes for gas separations have evolved rapidly in the past 25 years due to their easy processability for scale-up and low energy requirements. More than 90% of the membrane gas separation applications involve the separation of noncondensable gases such as carbon dioxide from methane, nitrogen from air, and hydrogen from nitrogen, argon or methane. Membrane gas separation is of special interest to petroleum producers and refiners, chemical companies, and industrial gas suppliers. Several applications of membrane gas separation have achieved commercial success, including carbon dioxide removal from natural gas and biogas and in enhanced oil recovery.

US 20090277837 A1 by Liu et al. provided a fluoropolymer coated membrane where the porous asymmetric membrane layer was coated directly by a thin layer of a hydrophobic fluoropolymer to improve the selectivity of the gas separation membrane. The coating of such coated membranes comprising hydrophobic fluoropolymer segments, however, may be subject to delamination by liquid hydrocarbon contaminants in the natural gas feed such as BTEX for natural gas upgrading. Delamination will result in poor performance durability, reduced resistance to hydrocarbon contaminants and plasticization.

Almost all of the commercially available polymer membranes, such as CA, polyimide, and polysulfone membranes formed by phase inversion and solvent exchange methods have an asymmetric integrally skinned membrane structure. See U.S. Pat. No. 3,133,132. Such membranes are characterized by a thin, dense, selectively semipermeable surface "skin" and a less dense void-containing (or porous), non-selective support region, with pore sizes ranging from large in the support region to very small proximate to the "skin". The thin dense skin layer and the porous non-selective support layer are formed simultaneously from the same polymeric material. Therefore, the cost of a new asymmetric integrally skinned polymeric membrane could be very high when an expensive new polymeric membrane material is used.

TFC membranes have several advantages over asymmetric integrally skinned membranes. An inexpensive membrane material can be used as the bulk of the material in the porous non-selective support layer and an expensive or difficult to synthesize high performance polymer with good separation properties can be used for the asymmetric integrally skinned polyimide-containing selective layer of the TFC membranes.

The present invention discloses a co-cast thin film composite (TFC) flat sheet membrane comprising an asymmetric porous non-selective support layer with a thickness of 10-50 micrometers and an asymmetric integrally skinned polyimide-containing selective layer with a thickness of 5-40 micrometers on top of the support layer, wherein the asymmetric integrally skinned polyimide-containing selective layer comprises a porous non-selective polyimide-containing support layer with a thickness of about 5-40 micrometers and a relatively porous, thin, dense, polyimide-containing top skin layer with a thickness of 0.02-0.2 micrometers. The co-cast TFC flat sheet membrane described in the present invention may further comprise a hydrophobic fluoropolymer coating layer with a thickness of 0.02-1 micrometers on top of the relatively porous, thin, dense, polyimide-containing top skin layer for gas separations. In some cases, the relatively porous, thin, dense, polyimide-containing top skin layer of the co-cast TFC comprising hydrophobic fluoropolymer coating layer described in the present invention is further cross-linked under UV radiation to improve the selectivity. The co-cast TFC flat sheet membrane described in the present invention may further comprise a hydrophilic polymer and a metal salt inside the pores on the relatively porous, thin, dense, polyimide-containing top skin layer for olefin/paraffin separations. The term "relatively porous, thin, dense, polyimide-containing top skin layer" means the polyimide-containing top skin layer has some very small pores with an average pore diameter of less than 2 nm.

The co-cast TFC flat sheet membrane described in the present invention comprises an asymmetric porous non-selective support layer and an asymmetric integrally skinned polyimide-containing selective layer on top of the support layer wherein the asymmetric porous non-selective support layer comprises a non-polyimide polymer or a mixture of a non-polyimide polymer and a polyimide polymer wherein the weight ratio of the non-polyimide polymer to the polyimide polymer in the mixture is in a range of 20:1 to 2:1.

The co-cast TFC flat sheet membrane described in the present invention comprises an asymmetric porous non-selective support layer and an asymmetric integrally skinned polyimide-containing selective layer on top of the support layer wherein the asymmetric integrally skinned polyimide-containing selective layer comprises a polyimide polymer or a mixture of a non-polyimide polymer and a polyimide polymer wherein the weight ratio of the non-polyimide polymer to the polyimide polymer in the mixture is in a range of 10:1 to 1:10.

The co-cast TFC flat sheet membrane allows the use of higher cost, high performance polyimide polymers to form the asymmetric integrally skinned polyimide-containing selective layer and the use of cheaper, commercially available polymer to form the asymmetric porous non-selective support layer without any potential delamination issue. Therefore, the co-cast TFC flat sheet membrane has reduced cost compared to the asymmetric integrally-skinned, flat sheet, higher cost, high performance polymer membranes.

Selection of the membrane materials for the formation of the asymmetric porous non-selective support layer of the co-cast TFC flat sheet membrane described in the current invention may be made on the basis of the mechanical strength, compatibility with the polyimide material in the asymmetric integrally skinned polyimide-containing selective layer, as well as other factors dictated by the operating conditions for selective permeation. The asymmetric porous non-selective support layer of the co-cast TFC flat sheet membrane is preferably formed on a highly porous non-selective woven or non-woven polymeric fabric backing, and in some instances may be essentially self-supporting. The asymmetric porous non-selective support layer of the new co-cast TFC flat sheet membrane may provide essentially all of the structural support for the co-cast TFC flat sheet membrane and can provide little, if any, resistance to the passage of gases or liquids.

Generally, the asymmetric porous non-selective support layer of the new co-cast TFC flat sheet membrane described in the current invention is prepared from cellulosic polymers such as cellulose acetate and cellulose triacetate, other polymers such as polysulfone, polyethersulfone, polyetherimide, polyimide, polyacrylonitrile, or a mixture thereof. These polymers provide a range of properties such as low cost, good solubility in organic solvents, good mechanical stability, and ease of processability that are important for the phase inversion membrane fabrication process. Typical polymers for the formation of the asymmetric porous non-selective support layer of the new co-cast TFC flat sheet membrane described in the current invention may be selected from but is not limited to, polysulfone, sulfonated polysulfone, polyethersulfone, sulfonated polyethersulfone, polyimide, polyetherimide, polyacrylonitrile, cellulosic polymers such as cellulose acetate, cellulose triacetate, cellulose acetate-butyrate, cellulose propionate, ethyl cellulose, methyl cellulose, nitrocellulose, poly(arylene oxides) such as poly(phenylene oxide) and poly(xylene oxide), and mixtures of thereof.

Some preferred polymers that are suitable for the preparation of the asymmetric porous non-selective support layer of the new co-cast TFC flat sheet membrane described in the current invention include, but are not limited to polyetherimide, polyimide, polyethersulfone, polysulfone, polyacrylonitrile, cellulosic polymers such as cellulose acetate and cellulose triacetate, and mixtures thereof.

The non-polyimide polymer in the asymmetric porous non-selective support layer and the non-polyimide polymer in the asymmetric integrally skinned polyimide-containing selective layer of the co-cast TFC flat sheet membrane can be selected from the same polymer or different polymers. Preferably, the non-polyimide polymer in the asymmetric porous non-selective support layer and the non-polyimide polymer in the asymmetric integrally skinned polyimide-containing selective layer of the new co-cast TFC flat sheet membrane described in the present invention are polyethersulfone.

The polyimide in the asymmetric porous non-selective support layer and the polyimide in the asymmetric integrally skinned polyimide-containing selective layer of co-cast TFC flat sheet membrane may be the same or different from each other and may be selected from, but are not limited to, the group consisting of poly(2,2'-bis-(3,4-dicarboxyphenyl) hexafluoropropane dianhydride-3,3',5,5'-tetramethyl-4,4'-methylene dianiline) polyimide derived from a polycondensation reaction of 2,2'-bis-(3,4-dicarboxyphenyl) hexafluoropropane dianhydride (6FDA) with 3,3',5,5'-tetramethyl-4,4'-methylene dianiline (TMMDA), poly(3,3', 4,4'-diphenylsulfone tetracarboxylic dianhydride-3,3',5,5'-tetramethyl-4,4'-methylene dianiline) polyimide derived from the polycondensation reaction of 3,3',4,4'-diphenylsulfone tetracarboxylic dianhydride (DSDA) with TMMDA, poly(2,2'-bis-(3,4-dicarboxyphenyl)hexafluoropropane dianhydride-3,5-diaminobenzoic acid-3,3'-dihydroxy-4,4'-diamino-biphenyl) polyimides derived from a polycondensation reaction of 6FDA with a mixture of 3,5-diaminobenzoic acid (3,5-DBA) and 3,3'-dihydroxy-4,4'-diamino-biphenyl (HAB) and the molar ratio of 3,5-DBA to HAB may be in a range of 1:0 to 1:5, poly(2,2'-bis-(3,4-dicarboxyphenyl)hexafluoropropane dianhydride-3,5-diaminobenzoic acid-3,3',5,5'-tetramethyl-4,4'-methylene dianiline) polyimides derived from the polycondensation reaction of 6FDA and a mixture of 3,5-DBA and 3,3',5,5'-tetramethyl-4,4'-methylene dianiline (TMMDA) and the molar ratio of 3,5-DBA to TMMDA may be in a range of 1:0 to 1:5, poly(6FDA-3,5-DBA), poly(6FDA-HAB), poly(2,2'-bis-(3, 4-dicarboxyphenyl)hexafluoropropane dianhydride-3,3'-methylene-bis(6-aminobenzoic acid)-3,3',5,5'-tetramethyl-4,4'-methylene dianiline) polyimides derived from the polycondensation reaction of 6FDA and a mixture of 3,3'-methylene-bis(6-aminobenzoic acid) (MBA) and TMMDA and the molar ratio of MBA to TMMDA may be in a range of 1:0 to 1:5, poly(6FDA-MBA), poly(6FDA-MBA-HAB)s and the molar ratio of MBA to HAB may be in a range of 1:0 to 1:5, poly(3,3',4,4'-diphenylsulfone tetracarboxylic dianhydride-3,5-diaminobenzoic acid-3,3'-dihydroxy-4,4'-diamino-biphenyl) polyimides derived from a polycondensation reaction of DSDA with a mixture of 3,5-DBA and HAB and the molar ratio of 3,5-DBA to HAB may be in a range of 1:0 to 1:5, poly(DSDA-3,5-DBA-TMMDA)s and the molar ratio of 3,5-DBA to TMMDA may be in a range of 1:0 to 1:5, poly(DSDA-MBA-TMMDA)s and the molar ratio of MBA to TMMDA may be in a range of 1:0 to 1:5, poly(DSDA-MBA-HAB)s and the molar ratio of MBA to HAB may be in a range of 1:0 to 1:5, poly(DSDA-3,5-DBA), poly(DSDA-MBA), poly(DSDA-3,5-DBA-MBA)s and the molar ratio of 3,5-DBA to MBA may be in a range of 1:0 to 1:5, poly(3,3',4,4'-benzophenone tetracarboxylic dianhydride-pyromellitic dianhydride-3,5-diaminobenzoic acid-3,3'-dihydroxy-4,4'-diamino-biphenyl) polyimides derived from a polycondensation reaction of a mixture of 3,3',4,4'-benzophenone tetracarboxylic dianhydride (BTDA) and pyromellitic dianhydride (PMDA) with a mixture of 3,5-DBA and HAB and the molar ratio of 3,5-DBA to HAB may be in a range of 1:0 to 1:5 and the molar ratio of BTDA to PMDA may be in a range of 2:1 to 1:2, poly(BTDA-PMDA-MBA-HAB)s and the molar ratio of MBA to HAB may be in a range of 1:0 to 1:5 and the molar ratio of BTDA to PMDA may be in a range of 2:1 to 1:2, poly(BTDA-PMDA-MBA-TMMDA)s and the molar ratio of MBA to TMMDA may be in a range of 1:0 to 1:5 and the molar ratio of BTDA to PMDA may be in a range of 2:1 to 1:2, poly(BTDA-PMDA-3,5-DBA-TMMDA)s and the molar ratio of 3,5-DBA to TMMDA may be in a range of 1:0 to 1:5 and the molar ratio of BTDA to PMDA may be in a range of 2:1 to 1:2, poly(3,3',4,4'-benzophenone tetracarboxylic dianhydride-pyromellitic dianhydride-3,3',5,5'-tetramethyl-4,4'-methylene dianiline) polyimide derived from the polycondensation reaction of a mixture of BTDA and PMDA with TMMDA and the molar ratio of BTDA to PMDA may be in a range of 2:1 to 1:2, poly(3,3',4,4'-benzophenone tetracarboxylic dianhydride-pyromellitic dianhydride-2,4,6-trimethyl-1,3-phenylenediamine) polyimide derived from the polycondensation reaction of a mixture of BTDA and PMDA with 2,4,6-trimethyl-1,3-phenylenediamine (TMPDA) and the molar ratio of BTDA to PMDA may be in a range of 2:1 to 1:2, poly(3,3',4,4'-benzophenone tetracarboxylic dianhydride-pyromellitic dianhydride-2,4,6-trimethyl-1,3-phenylenediamine-2,4-toluenediamine) polyimide derived from the polycondensation reaction of a mixture of BTDA and PMDA with a mixture of TMPDA and 2,4-toluenediamine (2,4-TDA) and the molar ratio of BTDA to PMDA may be in a range of 2:1 to 1:2 and the molar ratio of TMPDA to 2,4-TDA may be in a range of 5:1 to 1:5 and blends thereof.

The co-cast TFC flat sheet membrane may further comprise a hydrophobic fluoropolymer coating layer with a thickness of 0.02-1 micrometers on top of the relatively porous, thin, dense, polyimide-containing top skin layer for gas separations. The layer of hydrophobic fluoropolymer on top of the relatively porous, thin, dense, polyimide-containing top skin layer can be formed from an organic solvent-soluble hydrophobic fluoropolymer with high gas permeability. The fluoropolymers have high thermal, chemical, mechanical and electrical stability, as well as high gas permeability. The fluoropolymer may be an amorphous fluoropolymer selected from the DuPont Teflon® AF family of amorphous fluoropolymers including Teflon® AF1600 and Teflon® AF2400, Fluor® Pel™ PFC 504A CoE5 and FluoroPel™ PFC 504A CoFS fluoropolymers from Cytonix Corporation. Teflon AF fluoropolymers include a fluoropolymer that is a homopolymer of 2,2-bistrifluoro-methyl-4, 5-difluoro-1,3-dioxole (PDD), and a fluoropolymer that is an amorphous copolymer of 2,2-bistrifluoro-methyl-4,5-difluoro-1,3-dioxole (PDD) with a complementary amount of another fluorine-containing monomer selected from the group consisting of tetrafluoroethylene (TFE), perfluoro (alkyl vinyl ether)s, hexafluoropropylene, vinylidene fluoride, and chlorotrifluoroethylene. Other fluoropolymers include a fluoropolymer that is an amorphous copolymer of 2,2-bistrifluoro-methyl-4,5-difluoro-1,3-dioxole (PDD) and tetrafluoroethylene (TFE), a fluoropolymer that is an amorphous copolymer of 2,2-bistrifluoro-methyl-4,5-difluoro-1, 3-dioxole (PDD) and tetrafluoroethylene (TFE) with 65 mol % of dioxole and a glass transition temperature of 160° C. (DuPont Teflon® AF1600) and a fluoropolymer that is an amorphous copolymer of 2,2-bistrifluoro-methyl-4,5-difluoro-1,3-dioxole (PDD) and tetrafluoroethylene (TFE) with 87 mol % of dioxole and a glass transition temperature of 240° C. (DuPont Teflon® AF2400). Another type of fluoropolymers used in the present invention is Hyflon AD fluoropolymers from Solvay Solexis including a fluoropolymer that is a copolymer of 2,2,4-trifluoro-5-trifluoromethoxy-1,3-dioxole (TTD) and tetrafluoroethylene (TFE) and a fluoropolymer that is a copolymer of 2,2,4-trifluoro-5-trifluoromethoxy-1,3-dioxole (TTD) and tetrafluoroethylene (TFE) with 80 mol % of TTD and 20 mol % of TFE. Fluoropolymers from Cytonix Corporation that can also be used in the present invention include a fluoropolymer that is a fluoro-silane fluorinated copolymer with silane functional groups and a fluoropolymer that is a fluoro-epoxide fluorinated oligomer with epoxide functional groups.

The organic solvents that can be used for dissolving the fluoropolymer in the present invention are essentially perfluorinated solvents and mixtures thereof such as Fluorinert FC-75 (perfluoro(n-butyltetrahydrofuran)), Fluorinert FC-72, Fluorinert FC-770, and Fluorinert FC-40 (perfluoro (alkyl amine)). It is preferred that the fluoropolymer is diluted in the perfluorinated organic solvent or mixtures thereof in a concentration of from about 0.01 to about 10 wt %.

In some cases, the co-cast TFC flat sheet membranes comprising an asymmetric porous non-selective support layer, an asymmetric integrally skinned polyimide-containing selective layer, and a hydrophobic fluoropolymer coating layer in the present invention have undergone an additional UV cross-linking process. The polyimide with UV cross-linkable functional groups in the asymmetric integrally skinned polyimide-containing selective layer in the present invention comprises polymer chain segments where at least part of these polymer chain segments are cross-linked to each other through possible direct covalent bonds by exposure to UV radiation. The cross-linking of co-cast TFC flat sheet membranes provides membranes with superior selectivity and improved chemical and thermal stabilities compared to the corresponding uncross-linked co-cast TFC flat sheet membranes. Optimization of the cross-linking degree of the co-cast TFC flat sheet membranes described in the present invention will promote the tailoring of the co-cast TFC flat sheet membranes for a wide range of gas and liquid separations with improved permeation properties and environmental stability. The cross-linking degree of the co-cast TFC flat sheet membranes of the present invention can be controlled by adjusting the distance between the UV lamp and the membrane surface, UV radiation time, wavelength and strength of UV light, etc. Preferably, the distance from the UV lamp to the membrane surface is in the range of 0.8 to 25.4 cm (0.3 to 10 inches) with a UV light provided from 12 watt to 450 watt low pressure or medium pressure mercury arc lamp, and the UV radiation time is in the range of 0.5 min to 1 h. More preferably, the distance from the UV lamp to the membrane surface is in the range of 1.3 to 5.1 cm (0.5 to 2 inches) with a UV light provided from 12 watt to 450 watt low pressure or medium pressure mercury arc lamp, and the UV radiation time is in the range of 1 to 40 minutes.

The new co-cast TFC flat sheet membrane described in the present invention may further comprise a hydrophilic polymer and a metal salt inside the pores on the relatively porous, thin, dense, polyimide-containing top skin layer for olefin/paraffin separations. The incorporation of the hydrophilic polymer such as chitosan and hyaluronic acid inside the pores on the relatively porous, thin, dense, polyimide-containing top skin layer of the co-cast TFC flat sheet membrane reduces the pore size and also stabilize the metal salt such as silver nitrate inside the pores due to the complexation or chelating between the metal cations and the functional groups such as hydroxyl groups on the hydrophilic polymers. The hydrophilic polymer-containing pores in the co-cast TFC flat sheet membrane fix and stabilize the metal salts such as silver nitrate to prevent the loss of the metal salts from the membrane under the applied feed pressure. Therefore, the new co-cast TFC flat sheet membrane with a hydrophilic polymer and a metal salt inside the pores on the relatively porous, thin, dense, polyimide-containing top skin layer described in the present invention have shown high olefin/paraffin selectivity and very stable performance for olefin/paraffin separations.

The preferred hydrophilic polymer in the new co-cast TFC flat sheet membrane described in the present invention can be selected from, but is not limited to, a group of polymers containing chitosan, sodium carboxylmethyl-chitosan, carboxylmethyl-chitosan, hyaluronic acid, carbopol, polycarbophil calcium, poly(acrylic acid) (PAA), poly (methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The metal salts inside the pores on the relatively porous, thin, dense, polyimide-containing top skin layer of the co-cast TFC flat sheet membrane described in the current invention are preferred to be selected from silver salts or copper salts, such as silver (I) nitrate or copper (I) chloride.

The present invention also provides a method of making the new co-cast TFC flat sheet membrane comprising an asymmetric porous non-selective support layer with a thickness of 10-50 micrometers and an asymmetric integrally skinned polyimide-containing selective layer with a thickness of 5-40 micrometers on top of the support layer by simultaneously co-casting a polymer solution for the formation of the asymmetric porous non-selective support layer and a different polymer solution for the formation of the asymmetric integrally skinned polyimide-containing selective layer on top of the support layer using two casting knives via a phase inversion process. The method comprises: (a) preparing a homogeneous polyimide-containing casting dope solution for the formation of the asymmetric integrally skinned polyimide-containing selective layer, wherein said homogeneous polyimide-containing casting dope solution comprises an aromatic polyimide polymer or a mixture of an aromatic polyimide polymer and a non-polyimide polymer with the weight ratio of said aromatic polyimide polymer to said non-polyimide polymer of 10:1 to 1:10, solvents which can dissolve said aromatic polyimide polymer and said non-polyimide polymer, and non-solvents which cannot dissolve said aromatic polyimide polymer and said non-polyimide polymer; (b) preparing a homogeneous low cost polymer casting dope solution for the formation of the asymmetric porous non-selective support layer, wherein said homogeneous low cost polymer casting dope solution comprises a low cost non-polyimide polymer or a mixture of a low cost non-polyimide polymer and an aromatic polyimide polymer with the weight ratio of said non-polyimide polymer to said aromatic polyimide polymer of 20:1 to 2:1, solvents which can dissolve said non-polyimide polymer and said aromatic polyimide polymer, and non-solvents which cannot dissolve said non-polyimide polymer and said aromatic polyimide polymer; (c) forming co-cast thin film composite (TFC) membrane comprising an asymmetric porous non-selective support layer with a thickness of 10-50 micrometers and an asymmetric integrally skinned polyimide-containing selective layer with a thickness of 5-40 micrometers on top of said support layer by co-casting said homogeneous polyimide-containing casting dope solution and said homogeneous low cost polymer casting dope solution simultaneously on a highly porous non-selective fabric backing at a certain casting speed from 2 fpm to 15 fpm at a certain temperature from room temperature to 80° C. using two casting knives and a phase inversion technique including evaporating, coagulating, annealing, and washing steps. The casting knife with a knife gap from the bottom knife surface to the fabric backing surface of 100-500 µm for casting said homogeneous polyimide-containing casting dope solution for the formation of the asymmetric integrally skinned polyimide-containing selective layer with a thickness of 5-40 micrometers was set in front of the casting knife with a knife gap from the bottom knife surface to the fabric backing surface of 70-480 µm for casting said homogeneous low cost polymer casting dope solution for the formation of the asymmetric porous non-selective support layer with a thickness of 10-50 micrometers; (d) in some cases, an aqueous solution comprising a water soluble hydrophilic polymer such as chitosan or sodium alginate with a concentration in a range of 50 ppm to 5000 ppm was nipped onto the surface of the wet co-cast TFC membrane under tension at the end of the co-casting process to form co-cast TFC membrane comprising water soluble polymer inside the pores on the surface of the asymmetric integrally skinned polyimide-containing selective layer; (e) in some cases, the wet co-cast TFC membrane was dried at certain temperature from 50° to 100° C. to form dried co-cast TFC membrane.

In the case of gas separation applications, a thin, nonporous, hydrophobic polymer layer such as a fluoropolymer layer is coated on top of the asymmetric integrally skinned polyimide-containing selective layer of the co-cast TFC membrane via any coating method such as dip-coating, meniscus coating, nipping, spin coating, casting, soaking, spraying, painting, or other known conventional solution coating method using a fluoro solvent solution of the hydrophobic polymer with a concentration in a range of 0.01 to 10 wt %. The hydrophobic polymer coated co-cast TFC membrane can be further cross-linked under UV radiation.

For olefin/paraffin separation applications, a hydrophilic polymer is incorporated into the pores on the relatively porous, thin, dense, polyimide-containing top skin layer of the co-cast TFC flat sheet membrane by nipping of an aqueous solution of a hydrophilic polymer with a concentration in a range of 0.05 to 5 wt % at the end of the TFC membrane co-casting process or via the addition of the hydrophilic polymer to the gelation water tank during the TFC membrane co-casting fabrication process. The surface of the hydrophilic polymer-incorporated co-cast TFC flat sheet membrane is impregnated with an aqueous solution of a metal salt such as silver nitrate ($AgNO_3$) with a concentration in a range of 0.2M to 10M for a desired time in a range from 1 min to 48 h to form the co-cast TFC flat sheet membrane comprising a hydrophilic polymer and a metal salt inside the pores on the relatively porous, thin, dense, polyimide-containing top skin layer. The co-cast TFC flat sheet membrane prepared by co-casting method and used for the preparation of the co-cast TFC flat sheet membrane comprising a hydrophilic polymer and a metal salt inside the pores on the relatively porous, thin, dense, polyimide-containing top skin layer for olefin/paraffin separations described in the present invention has an intermediate less porous layer formed between the top asymmetric integrally skinned polyimide-containing selective layer and the bottom asymmetric porous non-selective support layer, which will improve the stability of the membrane for olefin/paraffin separations. The method of making the co-cast TFC flat sheet membrane comprising a hydrophilic polymer and a metal salt inside the pores on the relatively porous, thin, dense, polyimide-containing top skin layer for olefin/paraffin separations described in the present invention comprises: (1) preparing a co-cast TFC flat sheet membrane comprising a hydrophilic polymer such as chitosan or sodium alginate inside the pores on the relatively porous, thin, dense, polyimide-containing top skin layer as described in steps (a) to (d) in the present invention; (2) soaking the skin layer surface of the co-cast TFC flat sheet membrane comprising a hydrophilic polymer inside the pores on the relatively porous, thin, dense, polyimide-containing top skin layer in an aqueous solution of a metal salt such as silver nitrate ($AgNO_3$) with a concentration in a range of 0.5 M to 10 M, or in an aqueous solution of a metal salt such as silver nitrate and hydrogen peroxide for a certain time to form the co-cast TFC flat sheet membrane wherein the pores on the relatively porous, thin, dense, polyimide-containing top skin layer of the membrane comprise a hydrophilic polymer such as chitosan or sodium alginate, a metal salt such as silver nitrate, or a mixture of a metal salt such as silver nitrate and hydrogen peroxide.

The solvents used for dissolving the polymer materials for the preparation of the co-cast TFC flat sheet membranes are chosen primarily for their ability to completely dissolve the polymers and for ease of solvent removal in the membrane formation steps. Other considerations in the selection of solvents include low toxicity, low corrosive activity, low environmental hazard potential, availability and cost. Representative solvents include most amide solvents that are typically used for the formation of the co-cast TFC flat sheet membrane, such as N-methylpyrrolidone (NMP) and N,N-dimethyl acetamide (DMAc), methylene chloride, tetrahydrofuran (THF), acetone, methyl acetate, isopropanol, n-octane, n-hexane, n-decane, methanol, ethanol, N,N-dimethylformamide (DMF), dimethyl sulfoxide (DMSO), lactic acid, citric acid, dioxanes, 1,3-dioxolane, mixtures thereof, others known to those skilled in the art and mixtures thereof.

The co-cast TFC flat sheet membrane with a hydrophobic fluoropolymer coating layer and cross-linked under UV radiation has the advantages of low cost, high selectivity, as well as stable permeance (or flux) and sustained selectivity over time by resistance to solvent swelling, plasticization and liquid hydrocarbon contaminants for gas separation applications. The co-cast TFC flat sheet membrane with a hydrophilic polymer and a metal salt inside the pores on the relatively porous, thin, dense, polyimide-containing top skin layer has the advantages of low cost, high selectivity, and stable permeance (or flux) for olefin/paraffin separations.

The present invention discloses a process of using the co-cast TFC flat sheet membrane for gas separations and olefin/paraffin separations, such as natural gas liquid (NGL) recovery and $CO_2$ removal from natural gas in one-step, fuel gas conditioning, hydrogen recovery, natural gas upgrading applications such as off-shore gas-processing platforms, floating liquefied natural gas (FLNG), and floating, processing, storage and offloading (FPSO) vessel applications, as well as propylene/propane ($C_3=/C_3$) and ethylene/ethane ($C_2=/C_2$) separations. The invention provides a process for separating at least one gas from a mixture of gases using the new co-cast TFC flat sheet membrane with a hydrophobic fluoropolymer coating layer and cross-linked under UV radiation, the process comprising: (a) providing a co-cast TFC flat sheet membrane with a hydrophobic fluoropolymer coating layer and cross-linked under UV radiation which is permeable to at least one gas; (b) contacting the mixture on one side of the co-cast TFC flat sheet membrane with a hydrophobic fluoropolymer coating layer and cross-linked under UV radiation to cause at least one gas to permeate the co-cast TFC flat sheet membrane with a hydrophobic fluoropolymer coating layer and cross-linked under UV radiation; and (c) removing from the opposite side of the membrane a permeate gas composition comprising a portion of the at least one gas which permeated the membrane.

The present invention also provides a process for separating olefin from a mixture of olefin and paraffin using the new co-cast TFC flat sheet membrane comprising a hydrophilic polymer and a metal salt inside the pores on the relatively porous, thin, dense, polyimide-containing top skin layer described in the present invention, the process comprising: (a) providing a new stable high selectivity co-cast TFC flat sheet membrane comprising a hydrophilic polymer and a metal salt inside the pores on the relatively porous, thin, dense, polyimide-containing top skin layer described in the present invention which is permeable to the olefin; (b) contacting the humidified olefin/paraffin mixture feed on one side of the membrane to cause the olefin to permeate the membrane; and (c) removing from the opposite side of the membrane a permeate gas composition comprising a portion of the olefin which permeated through the membrane.

The co-cast TFC flat sheet membranes of the present invention are especially useful in the purification, separation or adsorption of a particular species in the liquid or gas phase. In addition to separation of pairs of gases, the co-cast TFC flat sheet membrane may, for example, be used for natural gas liquid (NGL) recovery and $CO_2$ removal from natural gas in one-step as well as natural gas upgrading applications such as FLNG and FPSO applications. The co-cast TFC flat sheet membrane may also be used for the purification of water or for the separation of proteins or other thermally unstable compounds, e.g. in the pharmaceutical and biotechnology industries. The co-cast TFC flat sheet membrane may also be used in fermenters and bioreactors to transport gases into the reaction vessel and transfer cell culture medium out of the vessel. Additionally, the co-cast TFC flat sheet membrane may be used for the removal of microorganisms from air or water streams, water purification, ethanol production in a continuous fermentation/membrane pervaporation system, and in detection or removal of trace compounds or metal salts in air or water streams.

The co-cast TFC flat sheet membranes are especially useful in gas separation processes in air purification, petrochemical, refinery, and natural gas industries. Examples of such separations include separation of volatile organic compounds (such as toluene, xylene, and acetone) from an atmospheric gas, such as nitrogen or oxygen and nitrogen recovery from air. Further examples of such separations are for the separation of $CO_2$ from natural gas, $H_2$ from $N_2$, $CH_4$, and Ar in ammonia purge gas streams, $H_2$ recovery in refineries, olefin/paraffin separations such as propylene/propane separation, and iso/normal paraffin separations. Any given pair or group of gases that differ in molecular size, for example nitrogen and oxygen, carbon dioxide and methane, hydrogen and methane or carbon monoxide, helium and methane, can be separated using the co-cast TFC flat sheet membrane described herein. More than two gases can be removed from a third gas. For example, some of the gas components which can be selectively removed from a raw natural gas using the membrane described herein include carbon dioxide, oxygen, nitrogen, water vapor, hydrogen sulfide, helium, and other trace gases. Some of the gas components that can be selectively retained include hydrocarbon gases. When permeable components are acid components selected from the group consisting of carbon dioxide, hydrogen sulfide, and mixtures thereof and are removed from a hydrocarbon mixture such as natural gas, one module, or at least two in parallel service, or a series of modules may be utilized to remove the acid components. For example, when one module is utilized, the pressure of the feed gas may vary from 275 kPa to about 2.6 MPa (25 to 4000 psi). The differential pressure across the membrane can be as low as about 0.7 bar or as high as 145 bar (about 10 psi or as high as about 2100 psi) depending on many factors such as the particular membrane used, the flow rate of the inlet stream and the availability of a compressor to compress the permeate stream if such compression is desired. Differential pressure greater than about 145 bar (2100 psi) may rupture the membrane. A differential pressure of at least 7 bar (100 psi) is preferred since lower differential pressures may require more modules, more time and compression of intermediate product streams. The operating temperature of the process may vary depending upon the temperature of the feed stream and upon ambient temperature conditions. Preferably, the effective operating temperature of the co-cast TFC flat sheet membrane of the present invention will range from about −50° to about 100° C. More preferably, the effective operating temperature of the co-cast TFC flat sheet membrane of the present invention will range from about −20° to about 70° C., and most preferably, the effective operating temperature of the co-cast TFC flat sheet membrane of the present invention will be less than about 70° C.

The co-cast TFC flat sheet membrane is also especially useful in gas/vapor separation processes in chemical, petrochemical, pharmaceutical and allied industries for removing organic vapor or liquid from gas streams, e.g. in off-gas treatment for recovery of volatile organic compounds to meet clean air regulations, or within process streams in production plants so that valuable compounds (e.g., vinylchloride monomer, propylene) may be recovered. Further examples of gas/vapor separation processes in which the co-cast TFC flat sheet membrane may be used are hydrocarbon vapor separation from hydrogen in oil and gas refineries, for hydrocarbon dew pointing of natural gas (i.e. to decrease the hydrocarbon dew point to below the lowest possible export pipeline temperature so that liquid hydrocarbons do not separate in the pipeline), for control of methane number in fuel gas for gas engines and gas turbines, and for gasoline recovery. The co-cast TFC flat sheet membrane may incorporate a species that adsorbs strongly to certain gases (e.g. cobalt porphyrins or phthalocyanines for $O_2$ or silver (I) for ethane) to facilitate their transport across the membrane.

The co-cast TFC flat sheet membrane may also be used in the separation of liquid mixtures by pervaporation, such as in the removal of organic compounds (e. g., alcohols, phenols, chlorinated hydrocarbons, pyridines, ketones) from water such as aqueous effluents or process fluids. A co-cast TFC flat sheet membrane which is ethanol-selective would be used to increase the ethanol concentration in relatively dilute ethanol solutions (5-10% ethanol) obtained by fermentation processes. Another liquid phase separation example using co-cast TFC flat sheet membrane is the deep desulfurization of gasoline and diesel fuels by a pervaporation membrane process similar to the process described in U.S. Pat. No. 7,048,846, incorporated by reference herein in its entirety. The co-cast TFC flat sheet membrane that is selective to sulfur-containing molecules would be used to selectively remove sulfur-containing molecules from fluid catalytic cracking (FCC) and other naphtha hydrocarbon streams. Further liquid phase examples include the separation of one organic component from another organic component, e. g. to separate isomers of organic compounds. Mixtures of organic compounds which may be separated using the co-cast TFC flat sheet membrane include: ethylacetate-ethanol, diethylether-ethanol, acetic acid-ethanol, benzene-ethanol, chloroform-ethanol, chloroform-methanol, acetone-isopropylether, allylalcohol-allylether, allylalcohol-cyclohexane, butanol-butylacetate, butanol-1-butylether, ethanol-ethylbutylether, propylacetate-propanol, isopropylether-isopropanol, methanol-ethanol-isopropanol, and ethylacetate-ethanol-acetic acid.

The co-cast TFC flat sheet membrane may be used for separation of organic molecules from water (e.g. ethanol and/or phenol from water by pervaporation) and removal of metal and other organic compounds from water. An additional application of the co-cast TFC flat sheet membrane is in chemical reactors to enhance the yield of equilibrium-limited reactions by selective removal of a specific product in an analogous fashion to the use of the co-cast TFC flat sheet membrane to enhance esterification yield by the removal of water.

The co-cast TFC flat sheet membrane has immediate applications for the separation of gas mixtures including carbon dioxide removal from natural gas. The co-cast TFC flat sheet membrane permits carbon dioxide to diffuse through at a faster rate than the methane in the natural gas. Carbon dioxide has a higher permeation rate than methane because of higher solubility, higher diffusivity, or both. Thus, carbon dioxide enriches on the permeate side of the membrane, and methane enriches on the feed (or reject) side of the membrane.

Any given pair of gases that differ in size, for example, nitrogen and oxygen, carbon dioxide and methane, carbon dioxide and nitrogen, hydrogen and methane or carbon monoxide, helium and methane, can be separated using the co-cast TFC flat sheet membrane described herein. More than two gases can be removed from a third gas. For example, some of the components which can be selectively removed from a raw natural gas using the co-cast TFC flat sheet membrane described herein include carbon dioxide, oxygen, nitrogen, water vapor, hydrogen sulfide, helium, and other trace gases. Some of the components that can be selectively retained include hydrocarbon gases.

EXAMPLES

The following examples are provided to illustrate one or more preferred embodiments of the invention, but are not limited embodiments thereof. Numerous variations can be made to the following examples that lie within the scope of the invention.

Example 1

Preparation of poly(3,3',4,4'-diphenylsulfone tetracarboxylic dianhydride-3,3',5,5'-tetramethyl-4,4'-methylene dianiline)/PES TFC Flat Sheet Membrane Comprising Chitosan and $AgNO_3$ (Abbreviated as 3MAg+/poly(DSDA-TMMDA)/PES-Chitosan TFC)

A polyimide membrane casting dope containing poly(3,3',4,4'-diphenylsulfone tetracarboxylic dianhydride-3,3',5,5'-tetramethyl-4,4'-methylene dianiline) polyimide (abbreviated as poly(DSDA-TMMDA)) derived from the polycondensation reaction of 3,3',4,4'-diphenylsulfone tetracarboxylic dianhydride (DSDA) with 3,3',5,5'-tetramethyl-4,4'-methylene dianiline (TMMDA), N-methyl-2-pyrrolidone (NMP), 1,3-dioxolane, acetone, tert-butanol and n-octane and a polyethersulfone (PES) membrane casting dope containing PES, NMP, $LiNO_3$, and lactic acid were co-cast using two casting knives on a highly porous non-selective symmetric woven Nylon 6,6 fabric backing at a casting speed of 6 fpm at room temperature. Two casting knives were used and knife gaps of 7 mil and 3 mil were set for poly(DSDA-TMMDA) membrane casting dope and PES membrane casting dope, respectively. The casting knife for poly(DSDA-TMMDA) membrane casting dope was set in front of the casting knife for PES membrane casting dope. The co-cast membrane with a poly(DSDA-TMMDA) polyimide selective layer on top of a PES highly porous support layer was evaporated for 13 seconds to form the nascent poly(DSDA-TMMDA)/PES TFC membrane. The membrane was immersed into a cold water coagulation tank and then immersed into a hot water tank to remove the trace amount of organic solvents in the membrane. A 2000 ppm chitosan in 2 wt % of acetic acid aqueous solution was dripped onto the surface of the poly(DSDA-TMMDA)/PES TFC wet membrane under tension to form poly(DSDA-TMMDA)/PES TFC wet membrane comprising chitosan inside the pores on the relatively porous, thin, dense, poly(DSDA-TMMDA) top skin layer. Finally the wet membrane was wound up on a core roll. The aqueous chitosan solution concentration can be in a range of 50 ppm to 5000 ppm. The skin layer surface of the poly(DSDA-TMMDA)/PES TFC wet membrane comprising chitosan inside the pores on the relatively porous, thin, dense, poly(DSDA-TMMDA) top skin layer was immersed in an aqueous solution of $AgNO_3$ for 2.5 h and then the $AgNO_3$ aqueous solution was removed from the membrane surface to form poly(DSDA-TMMDA)/PES TFC membrane comprising chitosan and $AgNO_3$ inside the pores on the relatively porous, thin, dense, poly(DSDA-TMMDA) top skin layer. The concentration of the $AgNO_3$ solution can be in a range of 1M to 5M. For example, the poly(DSDA-TMMDA)/PES TFC wet membrane with 2000 ppm chitosan aqueous solution nipping and 3M $AgNO_3$ aqueous solution soaking is abbreviated as 3MAg+/poly(DSDA-TMMDA)/PES-Chitosan TFC.

Example 2

Preparation of poly(3,3',4,4'-diphenylsulfone tetracarboxylic dianhydride-3,3',5,5'-tetramethyl-4,4'-methylene dianiline)+PES/poly(3,3',4,4'-diphenylsulfone tetracarboxylic dianhydride-3,3',5,5'-tetramethyl-4,4'-methylene dianiline)+PES TFC Flat Sheet Membrane Comprising Chitosan and $AgNO_3$ (Abbreviated as 3MAg+/poly(DSDA-TMMDA)+PES/poly(DSDA-TMMDA)+PES-Chitosan TFC)

A polyimide and PES blend membrane casting dope containing poly(DSDA-TMMDA), PES (poly(DSDA-TM- MDA):PES=1:1 weight ratio), NMP, 1,3-dioxolane, acetone, isopropanol and n-octane for the formation of a poly(DSDA-TMMDA)/PES (1:1) blend selective layer and a poly(DSDA-TMMDA) and PES blend membrane casting dope containing poly(DSDA-TMMDA), PES (poly(DSDA-TMMDA):PES=1:9 weight ratio), NMP, $LiNO_3$, and lactic acid for the formation of the highly porous poly(DSDA-TMMDA)/PES (1:9) blend support layer were co-cast using two casting knives on a highly porous non-selective symmetric woven Nylon 6,6 fabric backing at a casting speed of 6 fpm at room temperature. Two casting knives were used and knife gaps of 7 mil and 3 mil were set for poly(DSDA-TMMDA)/PES (1:1) blend selective layer membrane casting dope and poly(DSDA-TMMDA)/PES (1:9) blend highly porous support layer membrane casting dope, respectively. The casting knife for poly(DSDA-TMMDA)/PES (1:1) blend selective layer casting dope was set in front of the casting knife for poly(DSDA-TMMDA)/PES (1:9) blend highly porous support layer casting dope. The co-cast membrane with a poly(DSDA-TMMDA)/PES (1:1) blend selective layer on top of a poly(DSDA-TMMDA)/PES (1:9) blend highly porous support layer was evaporated for 13 seconds to form the nascent poly(DSDA-TMMDA)+PES (1:1)/poly(DSDA-TMMDA)+PES (1:9) TFC membrane. The membrane was immersed into a cold water coagulation tank and then immersed into a hot water tank to remove the trace amount of organic solvents in the membrane. A 2000 ppm chitosan in 2 wt % of acetic acid aqueous solution was dripped onto the surface of the poly(DSDA-TMMDA)+PES (1:1)/poly(DSDA-TMMDA)+PES (1:9) TFC wet membrane under tension to form poly(DSDA-TMMDA)+PES (1:1)/poly(DSDA-TMMDA)+PES (1:9) TFC wet membrane comprising chitosan inside the pores on the relatively porous, thin, dense, poly(DSDA-TMMDA)/PES (1:1) top skin layer. Finally the wet membrane was wound up on a core roll. The aqueous chitosan solution concentration can be in a range of 50 ppm to 5000 ppm. The skin layer surface of the poly(DSDA-TMMDA)+PES (1:1)/poly(DSDA-TMMDA)+PES (1:9) TFC wet membrane comprising chitosan inside the pores on the relatively porous, thin, dense, poly(DSDA-TMMDA)/PES (1:1) top skin layer was immersed in an aqueous solution of $AgNO_3$ for 2.5 h and then the $AgNO_3$ aqueous solution was removed from the membrane surface to form poly(DSDA-TMMDA)+PES (1:1)/poly(DSDA-TMMDA)+PES (1:9) TFC membrane comprising chitosan and $AgNO_3$ inside the pores on the relatively porous, thin, dense, poly(DSDA-TMMDA)/PES (1:1) top skin layer. The concentration of the $AgNO_3$ solution can be in a range of 1M to 5M. For example, the poly(DSDA-TMMDA)+PES (1:1)/poly(DSDA-TMMDA)+PES (1:9) TFC wet membrane with 2000 ppm chitosan aqueous solution nipping and 3M $AgNO_3$ aqueous solution soaking is abbreviated as 3MAg+/poly(DSDA-TMMDA)+PES/poly(DSDA-TMMDA)+PES-Chitosan TFC.

Example 3

Olefin/Paraffin Separation Performance of 3MAg+/poly (DSDA-TMMDA)/PES-Chitosan TFC and 3MAg+/poly(DSDA-TMMDA)+PES/poly(DSDA-TMMDA)+PES-Chitosan TFC Flat Sheet Membranes Propylene/propane (C3=/C3) permeation experimental results (Table 1) demonstrate that the 3MAg+/poly(DSDA-TMMDA)/PES-Chitosan TFC flat sheet membrane disclosed in Example 1 in the present invention has high performance stability as well as both high C3=/C3 selectivity of 837 (1 h) and high C3=permeance of 110 GPU (1 h) for propylene (C3=)/propane (C3) separation under 50° C., 791 kPa (100 psig), 70% C3=/30% C3, 700 cc/min retentate flow rate testing conditions. The 3MAg+/poly(DSDA-TMMDA)+PES/poly(DSDA-TMMDA)+PES-Chitosan TFC flat sheet membrane disclosed in Example 2 also showed high performance stability as well as both high C3=/C3 selectivity of 308 (1 h) and high C3=permeance of 160 GPU (1 h) for C3=/C3 separation under 50° C., 791 kPa (100 psig), 30% C3=/70% C3, 700 cc/min retentate flow rate testing conditions (Table 1). The 3MAg+/poly(DSDA-TMMDA)/PES-Chitosan TFC flat sheet membrane disclosed in Example 1 in the present invention also showed high ethylene (C2=)/ethane (C2) selectivity of >1000 and high C2=permeance of 475 GPU under 50° C., 653 kPa (80 psig), C2= and C2 single gas testing conditions for C2=/C2 separation.

TABLE 1

$C_{3=}/C_3$ separation performance of 3MAg+/poly(DSDA-TMMDA)/PES-Chitosan TFC and 3MAg+/poly(DSDA-TMMDA) + PES/poly(DSDA-TMMDA) + PES-Chitosan TFC Flat Sheet Membranes

| Membrane | Retentate flow rate (cc/min) | $P_{C3=}/L$ (GPU) | $\alpha_{C3=/C3}$ |
|---|---|---|---|
| 3MAg+/poly(DSDA-TMMDA)/PES-Chitosan TFC | 700 | 110.0[a] | 837[a] |
| 3MAg+/poly(DSDA-TMMDA) + PES/poly(DSDA-TMMDA) + PES-Chitosan TFC | 700 | 160.4[b] | 308[b] |
| 3MAg+/poly(DSDA-TMMDA) + PES/poly(DSDA-TMMDA) + PES-Chitosan TFC | 200 | 137.5[b] | 600[b] |

[a]Tested at 50° C. under 791 kPa (100 psig), 70% $C_{3=}$/30% $C_3$ mixed vapor feed pressure;
[b]Tested at 50° C. under 791 kPa (100 psig), 30% $C_{3=}$/70% $C_3$ mixed vapor feed pressure.
[c]1 GPU = $2.7 \times 10^{-5}$ $m^3$ (STP)/$m^2 \cdot h \cdot kPa$.

Example 4

Preparation of AF1600-Coated, UV Cross-linked poly(DSDA-TMMDA)-PES/poly(DSDA-TMMDA)-PES TFC Flat Sheet Membrane A poly(DSDA-TMMDA) and PES (1:1) blend membrane casting dope comprising poly(DSDA-TMMDA), PES, NMP, 1,3-dioxolane, acetone, isopropanol, and n-octane with poly(DSDA-TMMDA)/PES weight ratio of 1:1 for the formation of the integrally skinned poly(DSDA-TMMDA)/PES blend selective layer and a poly(DSDA-TMMDA) and PES (1:9) blend membrane casting dope containing poly(DSDA-TMMDA), PES, NMP, $LiNO_3$, and lactic acid with poly(DSDA-TMMDA)/PES weight ratio of 1:9 for the formation of the asymmetric porous non-selective poly(DSDA-TMMDA)/PES support layer were co-cast on a highly porous non-selective symmetric woven Nylon 6,6 fabric backing at a casting speed of 6 fpm at room temperature. Two casting knives were used and knife gaps of 6 mil and 5 mil were set for poly(DSDA-TMMDA)/PES (1:1) blend membrane casting dope and poly(DSDA-TMMDA)/PES (1:9) membrane casting dope, respectively. The casting knife for poly(DSDA-TMMDA)/PES (1:1) membrane casting dope was set in front of the casting knife for poly (DSDA-TMMDA)/PES (1:9) membrane casting dope. The co-cast membrane with poly(DSDA-TMMDA)/PES (1:1) selective layer on top of poly(DSDA-TMMDA)/PES (1:9)

highly porous support layer was evaporated for 13 seconds to form the nascent poly(DSDA-TMMDA)+PES (1:1)/poly (DSDA-TMMDA)+PES (1:9) TFC flat sheet membrane. The membrane was immersed into a cold water coagulation tank and then immersed into a hot water tank to remove the trace amount of organic solvents in the membrane. The poly(DSDA-TMMDA)+PES (1:1)/poly(DSDA-TMMDA)+ PES (1:9) TFC flat sheet membrane was dried with a continuous drying machine at 70° C. at 2.0 fpm. The dried poly(DSDA-TMMDA)+PES (1:1)/poly(DSDA-TMMDA)+ PES (1:9) TFC flat sheet membrane was dip coated with a 0.5 wt % AF1600 polymer solution in Fluorinert FC-770 solvent and dried at 85° C. to form the dried 0.5% AF1600-coated poly(DSDA-TMMDA)+PES (1:1)/poly(DSDA-TMMDA)+PES (1:9) TFC flat sheet membrane. The dried 0.5% AF1600-coated poly(DSDA-TMMDA)+PES (1:1)/poly (DSDA-TMMDA)+PES (1:9) TFC flat sheet membrane was UV cross-linked via UV radiation for 4 minutes at 8 cm distance using a UV lamp with intensity of 1.45 mW/cm$^2$ to form 0.5% AF1600-coated poly(DSDA-TMMDA)+PES (1:1)/poly(DSDA-TMMDA)+PES (1:9)-4UV8 TFC flat sheet membrane (abbreviated as 0.5% AF1600-Coated poly (DSDA-TMMDA)+PES (1:1)/poly(DSDA-TMMDA)+PES (1:9)-4UV8 TFC). The dried poly(DSDA-TMMDA)+PES (1:1)/poly(DSDA-TMMDA)+PES (1:9) TFC flat sheet membrane was also dip coated with a 1 wt % AF1600 polymer solution in Fluorinert FC-770 solvent and dried at 85° C. to form the dried 1% AF1600-coated poly(DSDA-TMMDA)+PES (1:1)/poly(DSDA-TMMDA)+PES (1:9) TFC flat sheet membrane. The dried 1% AF1600-coated poly(DSDA-TMMDA)+PES (1:1)/poly(DSDA-TMMDA)+ PES (1:9) TFC flat sheet membrane was UV cross-linked via UV radiation for 4 minutes at 8 cm distance using a UV lamp with intensity of 1.45 mW/cm$^2$ to form 1% AF1600-coated poly(DSDA-TMMDA)+PES (1:1)/poly(DSDA-TMMDA)+ PES (1:9)-4UV8 TFC flat sheet membrane (abbreviated as 1% AF1600-Coated poly(DSDA-TMMDA)+PES (1:1)/poly (DSDA-TMMDA)+PES (1:9)-4UV8 TFC).

Example 5

CO$_2$/CH$_4$ Separation Performance of 0.5% AF1600-Coated Poly(DSDA-TMMDA)+PES (1:1)/Poly (DSDA-TMMDA)+PES (1:9)-4UV8 and 1% AF1600-Coated Poly(DSDA-TMMDA)+PES (1:1)/ Poly(DSDA-TMMDA)+PES (1:9)-4UV8 TFC Flat Sheet Membranes 76 mm (3 inch) diameter circles of 0.5% AF1600-coated poly(DSDA-TMMDA)+PES (1:1)/poly(DSDA-TMMDA)+ PES (1:9)-4UV8 and 1% AF1600-coated poly(DSDA-TMMDA)+PES (1:1)/poly(DSDA-TMMDA)+PES (1:9)-4UV8 TFC flat sheet membranes were evaluated for gas transport properties using a natural gas feed containing 10% CO$_2$ and 90% CH$_4$ at a feed pressure of 6996 kPa (1000 psig) at 50° C. Table 2 shows a comparison of CO$_2$ permeance (P$_{CO2}$/L) and CO$_2$/CH$_4$ selectivity ($\alpha_{CO2/CH4}$) of the 0.5% AF1600-coated poly(DSDA-TMMDA)+PES (1:1)/poly(DSDA-TMMDA)+PES (1:9)-4UV8 and 1% AF1600-coated poly (DSDA-TMMDA)+PES (1:1)/poly(DSDA-TMMDA)+PES (1:9)-4UV8 TFC flat sheet membranes of the present invention. The results in Table 2 show that 1% AF1600-coated poly(DSDA-TMMDA)+PES (1:1)/poly(DSDA-TMMDA)+ PES (1:9)-4UV8 TFC flat sheet membrane has higher CO$_2$/ CH$_4$ selectivity and lower CO$_2$ permeance than 0.5% AF1600-coated poly(DSDA-TMMDA)+PES (1:1)/poly (DSDA-TMMDA)+PES (1:9)-4UV8 TFC flat sheet membrane.

TABLE 2

CO$_2$/CH$_4$ separation performance of 0.5% AF1600-Coated Poly(DSDA-TMMDA) + PES (1:1)/Poly(DSDA-TMMDA) + PES(1:9)-4UV8 and 1% AF1600-Coated Poly(DSDA-TMMDA) + PES (1:1)/Poly(DSDA-TMMDA) + PES(1:9)-4UV8 TFC Flat Sheet Membranes[a]

| Membrane | P$_{CO2}$/L (GPU)[b] | $\alpha_{CO2/CH4}$ |
|---|---|---|
| 0.5% AF1600-Coated poly(DSDA-TMMDA) + PES (1:1)/poly(DSDA-TMMDA) + PES(1:9)-4UV8 TFC | 65.0 | 21.0 |
| 0.5% AF1600-Coated poly(DSDA-TMMDA) + PES (1:1)/poly(DSDA-TMMDA) + PES(1:9)-4UV8 TFC | 57.1 | 21.9 |

[a]Tested at 50° C. under 6996 kPa (1000 psig), 10% CO$_2$/90% CH$_4$ mixed gas pressure.
[b]1 GPU = 2.7 × 10$^{-5}$ m$^3$ (STP)/m$^2$ · h · kPa.

SPECIFIC EMBODIMENTS

While the following is described in conjunction with specific embodiments, it will be understood that this description is intended to illustrate and not limit the scope of the preceding description and the appended claims.

A first embodiment of the invention is a co-cast thin film composite flat sheet membrane comprising an asymmetric porous non-selective support layer and an asymmetric integrally skinned polyimide-containing selective layer on top of the asymmetric porous non-selective support layer wherein the asymmetric porous non-selective support layer comprises a non-polyimide polymer or a mixture of a non-polyimide polymer and a polyimide polymer and wherein the weight ratio of the non-polyimide polymer to the polyimide polymer in the mixture is in a range of 201 to 21. An embodiment of the invention is one, any or all of prior embodiments in this paragraph up through the first embodiment in this paragraph wherein the asymmetric porous non-selective support layer and the asymmetric integrally skinned polyimide-containing selective layer are formed simultaneously via a co-casting phase inversion process using two casting knives. An embodiment of the invention is one, any or all of prior embodiments in this paragraph up through the first embodiment in this paragraph wherein the asymmetric porous non-selective support layer comprises a polymer selected from the group consisting of polysulfone, sulfonated polysulfone, polyethersulfone, sulfonated polyethersulfone, polyetherimide, polyimide, polyacrylonitrile, cellulose acetate, cellulose triacetate, cellulose acetate-butyrate, cellulose propionate, ethyl cellulose, methyl cellulose, nitrocellulose, poly(phenylene oxide), poly(xylene oxide), and mixtures of thereof. An embodiment of the invention is one, any or all of prior embodiments in this paragraph up through the first embodiment in this paragraph wherein the asymmetric integrally skinned polyimide-containing selective layer and wherein the asymmetric porous non-selective support layer comprises polyethersulfone. An embodiment of the invention is one, any or all of prior embodiments in this paragraph up through the first embodiment in this paragraph wherein the polyimide is selected from the group consisting of poly(2,2'-bis-(3,4-dicarboxyphenyl)hexafluoropropane dianhydride-3,3',5,5'-tetramethyl-4,4'-methylene dianiline) polyimide, poly(3,3', 4,4'-diphenylsulfone tetracarboxylic dianhydride-3,3',5,5'-tetramethyl-4,4'-methylene dianiline) polyimide, poly(2,2'- bis-(3,4-dicarboxyphenyl)hexafluoropropane dianhydride-3,3'-dihydroxy-4,4'-diamino-biphenyl) polyimide, poly(2,2'-bis-(3,4-dicarboxyphenyl)hexafluoropropane dianhydride-3,5-diaminobenzoic acid-3,3'-dihydroxy-4,4'-diamino-biphenyl) polyimides, poly(2,2'-bis-(3,4-dicarboxyphenyl) hexafluoropropane dianhydride-3,5-diaminobenzoic acid-3,3',5,5'-tetramethyl-4,4'-methylene dianiline) polyimides, poly(2,2'-bis-(3,4-dicarboxyphenyl)hexafluoropropane dianhydride-3,3'-methylenebis(6-aminobenzoic acid)-3,3',5,5'-tetramethyl-4,4'-methylene dianiline) polyimides, poly(3,3',4,4'-diphenylsulfone tetracarboxylic dianhydride-3,5-diaminobenzoic acid-3,3'-dihydroxy-4,4'-diamino-biphenyl) polyimides, poly(3,3',4,4'-diphenylsulfone tetracarboxylic dianhydride-3,3'-methylene-bis(6-aminobenzoic acid)-3,3',5,5'-tetramethyl-4,4'-methylene dianiline)s, poly(3,3',4,4'-diphenylsulfone tetracarboxylic dianhydride-3,5-diaminobenzoic acid), poly(3,3',4,4'-diphenylsulfone tetracarboxylic dianhydride-3,3'-methylene-bis(6-aminobenzoic acid)), poly(3,3',4,4'-diphenylsulfone tetracarboxylic dianhydride-3,5-diaminobenzoic acid-3,3'-methylene-bis(6-aminobenzoic acid))s, poly(3,3',4,4'-benzophenone tetracarboxylic dianhydride-pyromellitic dianhydride-3,5-diaminobenzoic acid-3,3'-dihydroxy-4,4'-diamino-biphenyl) polyimides, poly(3,3',4,4'-benzophenone tetracarboxylic dianhydride-pyromellitic dianhydride-3,3'-methylene-bis(6-aminobenzoic acid)-3,3'-dihydroxy-4,4'-diamino-biphenyl) s, poly(3,3',4,4'-benzophenone tetracarboxylic dianhydride-pyromellitic dianhydride-3,3'-methylene-bis(6-aminobenzoic acid)-3,3',5,5'-tetramethyl-4,4'-methylene dianiline)s, poly(3,3',4,4'-benzophenone tetracarboxylic dianhydride-pyromellitic dianhydride-3,5-DBA-3,3',5,5'-tetramethyl-4,4'-methylene dianiline)s, poly(3,3',4,4'-benzophenone tetracarboxylic dianhydride-pyromellitic dianhydride-3,3',5,5'-tetramethyl-4,4'-methylene dianiline), poly(3,3',4,4'-benzophenone tetracarboxylic dianhydride-pyromellitic dianhydride-2,4,6-trimethyl-1,3-phenylenediamine), poly(3,3',4,4'-benzophenone tetracarboxylic dianhydride-pyromellitic dianhydride-2,4,6-trimethyl-1,3-phenylenediamine-2,4-toluenediamine). An embodiment of the invention is one, any or all of prior embodiments in this paragraph up through the first embodiment in this paragraph wherein the asymmetric integrally skinned polyimide-containing selective layer comprises a polyimide polymer or a mixture of a non-polyimide polymer and a polyimide polymer wherein the weight ratio of the non-polyimide polymer to the polyimide polymer in the mixture is in a range of 101 to 110. An embodiment of the invention is one, any or all of prior embodiments in this paragraph up through the first embodiment in this paragraph wherein on top of the asymmetric integrally skinned polyimide-containing selective layer is a hydrophobic fluoropolymer layer and wherein the asymmetric integrally skinned polyimide-containing selective layer is cross-linked under UV radiation. An embodiment of the invention is one, any or all of prior embodiments in this paragraph up through the first embodiment in this paragraph further comprising a hydrophilic polymer and a metal salt inside pores on a polyimide-containing top skin layer. An embodiment of the invention is one, any or all of prior embodiments in this paragraph up through the first embodiment in this paragraph wherein the hydrophilic polymer is selected from the group consisting of chitosan, sodium carboxylmethyl-chitosan, carboxylmethyl-chitosan, hyaluronic acid, carbopol, polycarbophil calcium, poly(acrylic acid), poly(methacrylic acid), sodium alginate, alginic acid, poly(vinyl alcohol), poly(ethylene oxide), poly(ethylene glycol), poly(vinylpyrrolidone), gelatin, carrageenan, sodium lignosulfonate, and mixtures thereof and wherein the metal salt is a silver salt or a copper salt.

A second embodiment of the invention is a process for separating at least one component from a mixture using a co-cast thin film composite flat sheet membrane, the process comprising (a) providing a co-cast thin film composite flat sheet membrane which is permeable to at least one component; (b) contacting the mixture on one side of the co-cast thin film composite flat sheet membrane to cause at least one component to permeate the co-cast thin film composite flat sheet membrane; and (c) removing from the opposite side of the membrane a permeate composition comprising a portion of the at least one component which permeated the membrane. An embodiment of the invention is one, any or all of prior embodiments in this paragraph up through the second embodiment in this paragraph wherein the co-cast thin film composite flat sheet membrane comprises a hydrophilic polymer and a metal salt inside the pores on a porous, thin, dense, polyimide-containing top skin layer which is permeable to an olefin; wherein the mixture comprises a humidified olefin/paraffin mixture and wherein the permeate gas composition comprises a portion of the olefin. An embodiment of the invention is one, any or all of prior embodiments in this paragraph up through the second embodiment in this paragraph wherein the co-cast thin film composite flat sheet membrane comprises a hydrophobic fluoropolymer coating layer and wherein the co-cast thin film composite flat sheet membrane is cross-linked under UV radiation. An embodiment of the invention is one, any or all of prior embodiments in this paragraph up through the second embodiment in this paragraph wherein the mixture is selected from the group consisting of air, $CO_2$ from natural gas, $H_2$ from $N_2$, $CH_4$, and Ar in ammonia purge gas streams, $H_2$ recovery in refinery gas streams, olefin/paraffin mixtures, and He recovery from natural gas. An embodiment of the invention is one, any or all of prior embodiments in this paragraph up through the second embodiment in this paragraph wherein the thin film composite flat sheet membrane comprises an asymmetric porous non-selective support layer and an asymmetric integrally skinned polyimide-containing selective layer on top of the asymmetric porous non-selective support layer wherein the asymmetric porous non-selective support layer comprises a non-polyimide polymer or a mixture of a non-polyimide polymer and a polyimide polymer and wherein the weight ratio of the non-polyimide polymer to the polyimide polymer in the mixture is in a range of 201 to 21. An embodiment of the invention is one, any or all of prior embodiments in this paragraph up through the second embodiment in this paragraph wherein the asymmetric porous non-selective support layer comprising a polymer selected from the group consisting of polysulfone, sulfonated polysulfone, polyethersulfone, sulfonated polyethersulfone, polyetherimide, polyimide, polyacrylonitrile, cellulose acetate, cellulose triacetate, cellulose acetate-butyrate, cellulose propionate, ethyl cellulose, methyl cellulose, nitrocellulose, poly(phenylene oxide), poly(xylene oxide), and mixtures of thereof. An embodiment of the invention is one, any or all of prior embodiments in this paragraph up through the second embodiment in this paragraph wherein the asymmetric integrally skinned polyimide-containing selective layer comprises a polyimide selected from the group consisting of poly(2,2'-bis-(3,4-dicarboxyphenyl)hexafluoropropane dianhydride-3,3',5,5'-tetramethyl-4,4'-methylene dianiline) polyimide, poly(3,3',4,4'-diphenylsulfone tetracarboxylic dianhydride-3,3',5,5'-tetramethyl-4,4'-methylene dianiline) polyimide, poly(2,2'-bis-(3,4-dicarboxyphenyl)

hexafluoropropane dianhydride-3,3'-dihydroxy-4,4'-diamino-biphenyl) polyimide, poly(2,2'-bis-(3,4-dicarboxyphenyl)hexafluoropropane dianhydride-3,5-diaminobenzoic acid-3,3'-dihydroxy-4,4'-diamino-biphenyl) polyimides, poly(2,2'-bis-(3,4-dicarboxyphenyl)hexafluoropropane dianhydride-3,5-diaminobenzoic acid-3,3',5,5'-tetramethyl-4,4'-methylene dianiline) polyimides, poly(2,2'-bis-(3,4-dicarboxyphenyl)hexafluoropropane dianhydride-3,3'-methylenebis(6-aminobenzoic acid)-3,3',5,5'-tetramethyl-4,4'-methylene dianiline) polyimides, poly(3,3',4,4'-diphenylsulfone tetracarboxylic dianhydride-3,5-diaminobenzoic acid-3,3'-dihydroxy-4,4'-diamino-biphenyl) polyimides, poly(3,3',4,4'-diphenylsulfone tetracarboxylic dianhydride-3,3'-methylene-bis(6-aminobenzoic acid)-3,3',5,5'-tetramethyl-4,4'-methylene dianiline)s, poly(3,3',4,4'-diphenylsulfone tetracarboxylic dianhydride-3,5-diaminobenzoic acid), poly(3,3',4,4'-diphenylsulfone tetracarboxylic dianhydride-3,3'-methylene-bis(6-aminobenzoic acid)), poly(3,3',4,4'-diphenylsulfone tetracarboxylic dianhydride-3,5-diaminobenzoic acid-3,3'-methylene-bis(6-aminobenzoic acid))s, poly(3,3',4,4'-benzophenone tetracarboxylic dianhydride-pyromellitic dianhydride-3,5-diaminobenzoic acid-3,3'-dihydroxy-4,4'-diamino-biphenyl) polyimides, poly(3,3',4,4'-benzophenone tetracarboxylic dianhydride-pyromellitic dianhydride-3,3'-methylene-bis(6-aminobenzoic acid)-3,3'-dihydroxy-4,4'-diamino-biphenyl)s, poly(3,3',4,4'-benzophenone tetracarboxylic dianhydride-pyromellitic dianhydride-3,3'-methylene-bis(6-aminobenzoic acid)-3,3',5,5'-tetramethyl-4,4'-methylene dianiline)s, poly(3,3',4,4'-benzophenone tetracarboxylic dianhydride-pyromellitic dianhydride-3,5-DBA-3,3',5,5'-tetramethyl-4,4'-methylene dianiline)s, poly(3,3',4,4'-benzophenone tetracarboxylic dianhydride-pyromellitic dianhydride-3,3',5,5'-tetramethyl-4,4'-methylene dianiline), poly(3,3',4,4'-benzophenone tetracarboxylic dianhydride-pyromellitic dianhydride-2,4,6-trimethyl-1,3-phenylenediamine), poly(3,3',4,4'-benzophenone tetracarboxylic dianhydride-pyromellitic dianhydride-2,4,6-trimethyl-1,3-phenylenediamine-2,4-toluenediamine).

A third embodiment of the invention is a method of making a co-cast thin film composite flat sheet membrane comprising an asymmetric porous non-selective support layer and an asymmetric integrally skinned polyimide-containing selective layer on top of the asymmetric porous non-selective support layer, comprising (a) preparing a homogeneous polyimide-containing casting dope solution for the formation of the asymmetric integrally skinned polyimide-containing selective layer; (b) preparing a homogeneous polymer casting dope solution for the formation of the asymmetric porous non-selective support layer; and (c) forming co-cast thin film composite membrane by simultaneously co-casting the homogeneous polyimide-containing casting dope solution and the homogeneous polymer casting dope solution on a highly porous non-selective fabric backing using two casting knives and a phase inversion process, wherein the casting knife for casting the homogeneous polyimide-containing casting dope solution is set in front of the casting knife for casting the homogeneous polymer casting dope solution, wherein the homogeneous polymer casting dope solution for the formation of the asymmetric porous non-selective support layer comprises a non-polyimide polymer or a mixture of a non-polyimide polymer and a polyimide polymer and wherein the weight ratio of the non-polyimide polymer to the polyimide polymer in the mixture is in a range of 201 to 21. An embodiment of the invention is one, any or all of prior embodiments in this paragraph up through the third embodiment in this paragraph further comprises a step of nipping an aqueous solution comprising a water soluble hydrophilic polymer onto the surface of the co-cast thin film composite membrane under tension to form a co-cast thin film composite membrane comprising the water soluble polymer inside the pores on the surface of the asymmetric integrally skinned polyimide-containing selective layer. An embodiment of the invention is one, any or all of prior embodiments in this paragraph up through the third embodiment in this paragraph further comprises soaking the skin layer surface of the co-cast thin film composite membrane comprising the water soluble polymer inside the pores on the surface of the asymmetric integrally skinned polyimide-containing selective layer in an aqueous solution of a metal salt selected from a silver salt or a copper salt. An embodiment of the invention is one, any or all of prior embodiments in this paragraph up through the third embodiment in this paragraph further comprises a step of coating a thin, nonporous, hydrophobic polymer layer on top of the asymmetric integrally skinned polyimide-containing selective layer.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A co-cast thin film composite flat sheet membrane comprising an asymmetric porous non-selective support layer and an asymmetric integrally skinned polyimide-containing selective layer on top of said asymmetric porous non-selective support layer wherein said asymmetric porous non-selective support layer comprises a non-polyimide polymer or a mixture of a non-polyimide polymer and a polyimide polymer, wherein on top of said asymmetric integrally skinned polyimide-containing selective layer is a hydrophobic fluoropolymer layer and wherein said asymmetric integrally skinned polyimide-containing selective layer is cross-linked under UV radiation and wherein the weight ratio of said non-polyimide polymer to said polyimide polymer in said mixture is in a range of 20:1 to 2:1.

2. The co-cast thin film composite flat sheet membrane of claim 1 wherein said asymmetric porous non-selective support layer and said asymmetric integrally skinned polyimide-containing selective layer are formed simultaneously via a co-casting phase inversion process using two casting knives.

3. The co-cast thin film composite flat sheet membrane of claim 1 wherein said asymmetric porous non-selective support layer comprises a polymer selected from the group consisting of polysulfone, sulfonated polysulfone, polyethersulfone, sulfonated polyethersulfone, polyetherimide, polyimide, polyacrylonitrile, cellulose acetate, cellulose triacetate, cellulose acetate-butyrate, cellulose propionate, ethyl cellulose, methyl cellulose, nitrocellulose, poly(phenylene oxide), poly(xylene oxide), and mixtures of thereof.

4. The co-cast thin film composite flat sheet membrane of claim 1 wherein said asymmetric integrally skinned polyimide-containing selective layer and wherein said asymmetric porous non-selective support layer comprises polyethersulfone.

5. The co-cast thin film composite flat sheet membrane of claim 1 wherein said polyimide is selected from the group consisting of poly(2,2'-bis-(3,4-dicarboxyphenyl)hexafluoropropane dianhydride-3,3',5,5'-tetramethyl-4,4'-methylene dianiline) polyimide, poly(3,3',4,4'-diphenylsulfone tetracarboxylic dianhydride-3,3',5,5'-tetramethyl-4,4'-methylene dianiline) polyimide, poly(2,2'-bis-(3,4-dicarboxyphenyl) hexafluoropropane dianhydride-3,3'-dihydroxy-4,4'-diamino-biphenyl) polyimide, poly(2,2'-bis-(3,4-dicarboxyphenyl)hexafluoropropane dianhydride-3,5-diaminobenzoic acid-3,3'-dihydroxy-4,4'-diamino-biphenyl) polyimides, poly(2,2'-bis-(3,4-dicarboxyphenyl)hexafluoropropane dianhydride-3,5-diaminobenzoic acid-3,3',5,5'-tetramethyl-4,4'-methylene dianiline) polyimides, poly(2,2'-bis-(3,4-dicarboxyphenyl)hexafluoropropane dianhydride-3,3'-methylenebis(6-aminobenzoic acid)-3,3',5,5'-tetramethyl-4,4'-methylene dianiline) polyimides, poly(3,3',4,4'-diphenylsulfone tetracarboxylic dianhydride-3,5-diaminobenzoic acid-3,3'-dihydroxy-4,4'-diamino-biphenyl) polyimides, poly(3,3',4,4'-diphenylsulfone tetracarboxylic dianhydride-3,3'-methylene-bis(6-aminobenzoic acid)-3,3', 5,5'-tetramethyl-4,4'-methylene dianiline)s, poly(3,3',4,4'-diphenylsulfone tetracarboxylic dianhydride-3,5-diaminobenzoic acid), poly(3,3',4,4'-diphenylsulfone tetracarboxylic dianhydride-3,3'-methylene-bis(6-aminobenzoic acid)), poly(3,3',4,4'-diphenylsulfone tetracarboxylic dianhydride-3,5-diaminobenzoic acid-3,3'-methylene-bis(6-aminobenzoic acid))s, poly(3,3',4,4'-benzophenone tetracarboxylic dianhydride-pyromellitic dianhydride-3,5-diaminobenzoic acid-3,3'-dihydroxy-4,4'-diamino-biphenyl) polyimides, poly(3,3',4,4'-benzophenone tetracarboxylic dianhydride-pyromellitic dianhydride-3,3'-methylene-bis(6-aminobenzoic acid)-3,3'-dihydroxy-4,4'-diamino-biphenyl) s, poly(3,3',4,4'-benzophenone tetracarboxylic dianhydride-pyromellitic dianhydride-3,3'-methylene-bis(6-aminobenzoic acid)-3,3',5,5'-tetramethyl-4,4'-methylene dianiline)s, poly(3,3',4,4'-benzophenone tetracarboxylic dianhydride-pyromellitic dianhydride-3,5-DBA-3,3',5,5'-tetramethyl-4,4'-methylene dianiline)s, poly(3,3',4,4'-benzophenone tetracarboxylic dianhydride-pyromellitic dianhydride-3,3',5,5'-tetramethyl-4,4'-methylene dianiline), poly(3, 3',4,4'-benzophenone tetracarboxylic dianhydride-pyromellitic dianhydride-2,4,6-trimethyl-1,3-phenylenediamine), poly(3,3',4,4'-benzophenone tetracarboxylic dianhydride-pyromellitic dianhydride-2,4,6-trimethyl-1,3-phenylenediamine-2,4-toluenediamine).

6. The co-cast thin film composite flat sheet membrane of claim 1 wherein said asymmetric integrally skinned polyimide-containing selective layer comprises a polyimide polymer or a mixture of a non-polyimide polymer and a polyimide polymer wherein the weight ratio of the non-polyimide polymer to the polyimide polymer in the mixture is in a range of 10:1 to 1:10.

7. A co-cast thin film composite flat sheet membrane comprising:
an asymmetric porous non-selective support layer;
an asymmetric integrally skinned polyimide-containing selective layer on top of said asymmetric porous non-selective support layer;
a hydrophilic polymer layer is on top of said asymmetric integrally skinned polyimide-containing selective layer and;
a metal salt inside pores on said asymmetric integrally skinned polyimide-containing top skin layer;
wherein said asymmetric porous non-selective support layer comprises a non-polyimide polymer or a mixture of a non-polyimide polymer and a polyimide polymer; and
wherein the weight ratio of said non-polyimide polymer to said polyimide polymer in said mixture is in a range of 20:1 to 2:1.

8. The co-cast thin film composite flat sheet membrane of claim 7 wherein said hydrophilic polymer is selected from the group consisting of chitosan, sodium carboxylmethyl-chitosan, carboxylmethyl-chitosan, hyaluronic acid, carbopol, polycarbophil calcium, poly(acrylic acid), poly (methacrylic acid), sodium alginate, alginic acid, poly(vinyl alcohol), poly(ethylene oxide), poly(ethylene glycol), poly(vinylpyrrolidone), gelatin, carrageenan, sodium lignosulfonate, and mixtures thereof and wherein said metal salt is a silver salt or a copper salt.

9. The co-cast thin film composite flat sheet membrane of claim 7 wherein said asymmetric porous non-selective support layer and said asymmetric integrally skinned polyimide-containing selective layer are formed simultaneously via a co-casting phase inversion process using two casting knives.

10. The co-cast thin film composite flat sheet membrane of claim 7 wherein on top of said asymmetric integrally skinned polyimide-containing selective layer is a hydrophobic fluoropolymer layer and wherein said asymmetric integrally skinned polyimide-containing selective layer is cross-linked under UV radiation.

* * * * *